United States Patent  
Bell et al.

(10) Patent No.: US 10,739,339 B2
(45) Date of Patent: Aug. 11, 2020

(54) PORTABLE MICROARRAY ASSEMBLY

(71) Applicant: Grace Bio-Labs, Inc., Bend, OR (US)

(72) Inventors: Florian Gene Bell, Bend, OR (US);
Jacob Burrel Wells, Bend, OR (US);
Donna Kay Barton, Bend, OR (US);
Jennipher Lyn Grudzien, Bend, OR (US)

(73) Assignee: Grace Bio-Labs, Inc., Bend, OR (US)

( * ) Notice: Subject to any disclaimer, the term of this patent is extended or adjusted under 35 U.S.C. 154(b) by 440 days.

(21) Appl. No.: 15/277,746

(22) Filed: Sep. 27, 2016

(65) Prior Publication Data

US 2017/0099415 A1   Apr. 6, 2017

Related U.S. Application Data

(60) Provisional application No. 62/236,671, filed on Oct. 2, 2015.

(51) Int. Cl.
G01N 21/00 (2006.01)
G01N 33/543 (2006.01)
G02B 27/14 (2006.01)
H04N 5/232 (2006.01)
H04N 5/225 (2006.01)

(52) U.S. Cl.
CPC ..... G01N 33/54366 (2013.01); G02B 27/141 (2013.01); H04N 5/23293 (2013.01); H04N 5/2254 (2013.01); H04N 5/2256 (2013.01)

(58) Field of Classification Search
CPC ........... G01N 21/6486; G01N 21/6456; G01N 21/6428

USPC ............................................ 422/82.05, 82.08
See application file for complete search history.

(56) References Cited

U.S. PATENT DOCUMENTS 6,362,004 B1    3/2002  Noblett
8,428,398 B2    4/2013  Thompson et al.
2007/0098596 A1 5/2007  Fries et al.

OTHER PUBLICATIONS

Hamilton, G. et al., "A large field CCD system for quantitative imaging of microarrays," Nucleic Acids Research, vol. 34, No. 8, May 2, 2006, 14 pages.
Thompson, D. et al., "An Adaptable, Portable Microarray Reader for Biodetection," Sensors, vol. 9, No. 4, Apr. 14, 2009, 14 pages.
"GenePix 4000B Microarray Scanner," Molecular Devices Data Sheet, Available Online at http://go.pardot.com/83942/2015-06-17/mwf/83942/3898/GenePix_4000B_datasheet_rev_B.pdf, Jun. 2010, 2 pages.

Primary Examiner — Natalia Levkovich
(74) Attorney, Agent, or Firm — McCoy Russell LLP

(57) ABSTRACT

Methods and systems are provided for imaging a microarray of a microarray assembly. The microarray assembly may be configured as a protein microarray and may be used to visualize protein expression levels in sample for disease detection and/or diagnosis. In one example, the microarray assembly may comprise a laser pointed in a first direction, a camera positioned parallel to and vertically below the laser, a first dichroic mirror vertically aligned with the laser for reflecting light emitted from the laser, a second mirror vertically aligned with the camera and horizontally aligned with the first dichroic mirror, and a chip coated in a nitrocellulose film and including an array of wells containing one or more biomolecules.

13 Claims, 8 Drawing Sheets

PORTABLE MICROARRAY ASSEMBLY

CROSS-REFERENCE TO RELATED APPLICATION

This application claims priority to U.S. Provisional Application No. 62/236,671, entitled "PORTABLE MICROARRAY ASSEMBLY," filed Oct. 2, 2015, the entire contents of which is hereby incorporated by reference for all purposes.

FIELD

The present description relates generally to systems and methods for imaging and analyzing biomolecule microarrays.

BACKGROUND/SUMMARY

Microarray systems may be used to detect and quantify biomolecules such as antibodies, antigens, oligonucleotides, and RNA for a variety of clinical purposes such as understanding gene expression, gene regulation, protein production, protein modification, etc. Biomolecules may be adhered to microarray spots or wells formed on a glass slide or chip, and a fluorescent label, such as an organic dye, may be bound to a target subset of the biomolecules. Light from a laser may be directed to the biomolecules, and those biomolecules tagged with the fluorescent label may emit light in response to excitation from the laser. In some examples, light emitted from the luminescent labels may be gathered by a lens system and an image of the illuminated biomolecules may be captured. The image may then be analyzed to quantify expressions levels of the target biomolecules. Specifically, the intensity of different wavelengths of light may be compared to determine the relative intensity of emissions at wavelengths associated with the fluorescent tags. Because the fluorescent tags are bound to the target biomolecules, biomolecule expression levels or concentrations in the samples being tested, may be inferred based on intensity levels of light produced by the fluorescent labels.

In one example, microarrays may be configured to measure protein levels. Specifically, protein microarrays may be configured to measure antibody levels in a sample (e.g., lysate, serological, blood, or synthetic samples). As such, protein microarrays may be used to identify and/or diagnose infectious diseases. Proteins (e.g., antigens) may be affixed to a nitrocellulose film coating on the chip. When incubated with patient samples (e.g., whole blood, serum, plasma, saliva) containing antibodies specific to the printed antigens, the antibodies may bind to the antigens on the array. Probe molecules tagged with the fluorescent label may then bind to the antibodies, illuminating the antibodies when exposed to the laser beam. A clinical diagnosis may be made based on antibody expression levels as inferred from the luminescence, and therefore concentration, of the fluorescent labels.

However, the inventors herein have recognized potential issues with current microarray systems. As one example, image acquisition in most microarray systems is accomplished by a laser scanner included in the microarray system. Laser scanners may be necessary to deliver images at high enough resolution qualities to make accurate biomolecule identification and quantification determinations. However, laser scanners are often very large, and as a result current microarray system are stationary and not transportable. Further, many microarray systems may include multiple laser scanners for wavelength multiplexing, increasing the size, weight, and expense of such microarray systems. Thus, samples including the biomolecules must be taken to the microarray and scanner for analysis. As such, it may take a significant amount of time to render a diagnosis due to the delay associated with transporting the sample from a patient to the microarray scanner.

In another example, diagnosis determination may be difficult due to the low sensitivity of the protein microarrays. Specifically, organic dyes used to fluorescently label the biomolecules may have relatively broad emission and absorption bands, resulting in increased amounts of background noise in the biomolecule images. Additionally, light emitted from the organic dyes may be of low intensity. Further, the dyes may be prone to optical fading (photo bleaching) after exposure to intense excitation light. As such, image resolution may be low, and differentiation and quantification of the biomolecules may be challenging, resulting in reduced accuracy of disease diagnoses in protein microarrays.

In one example, the issues described above may be addressed by a microarray assembly comprising a laser emitting in a first direction, a camera positioned parallel to and vertically below the laser, a first dichroic mirror horizontally aligned with the laser for reflecting light emitted from the laser, a second mirror horizontally aligned with the camera and vertically aligned with the first dichroic mirror, and a chip coated in a nitrocellulose film and including an array of wells containing one or more biomolecules. In this way, the size of the microarray may be reduced by utilizing a camera instead of a laser scanner for acquiring an image of the wells. The size may be further reduced by positioning the camera and laser in parallel with one another, thereby increasing the portability of the microarray.

In some examples, the assembly may further include a cuvette for housing the chip, the cuvette including one or more of an aperture and groove for receiving the chip. The cuvette may additionally include an optically clear window integrally forming a front wall of the cuvette. The front wall of the cuvette may be pointed towards the first dichroic mirror for receiving a light beam produced from the laser. By including the cuvette for the chip, instances of contamination may be reduced.

In other examples, the biomolecules may be tagged with a fluorescent label, where the fluorescent label may comprise Quantum Nanocrystal fluorescent-nanoparticles (QNC). By using QNC to label the biomolecules as opposed to organic dyes, the sensitivity and resolution of the images captured by the microarray may be increased, allowing for improved accuracy in the diagnosis of infectious diseases.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
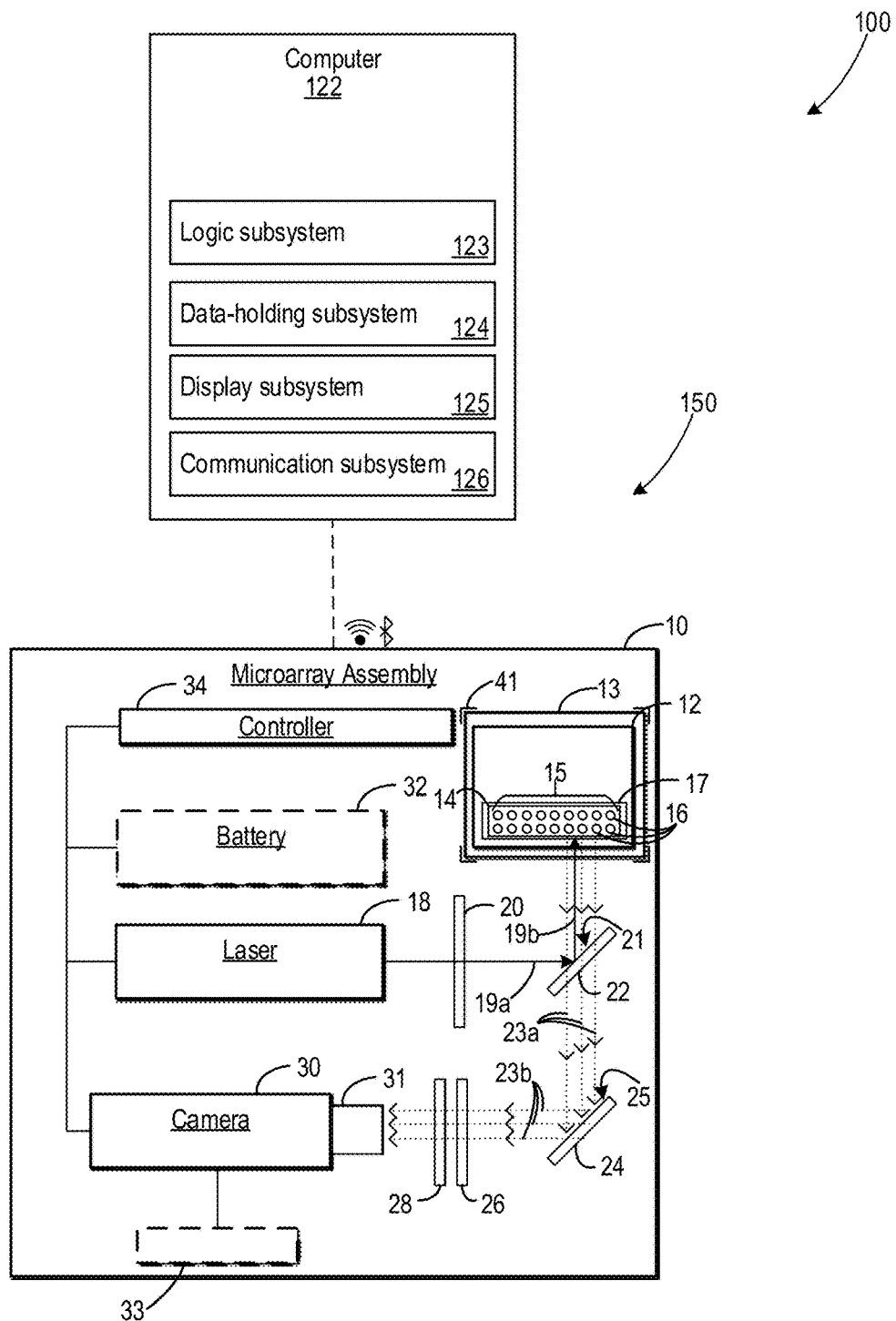
FIG. 1 shows a schematic of a biomolecule analysis system for quantifying biomolecule levels, the analysis system including a biomolecule microarray assembly.
Figure 6:
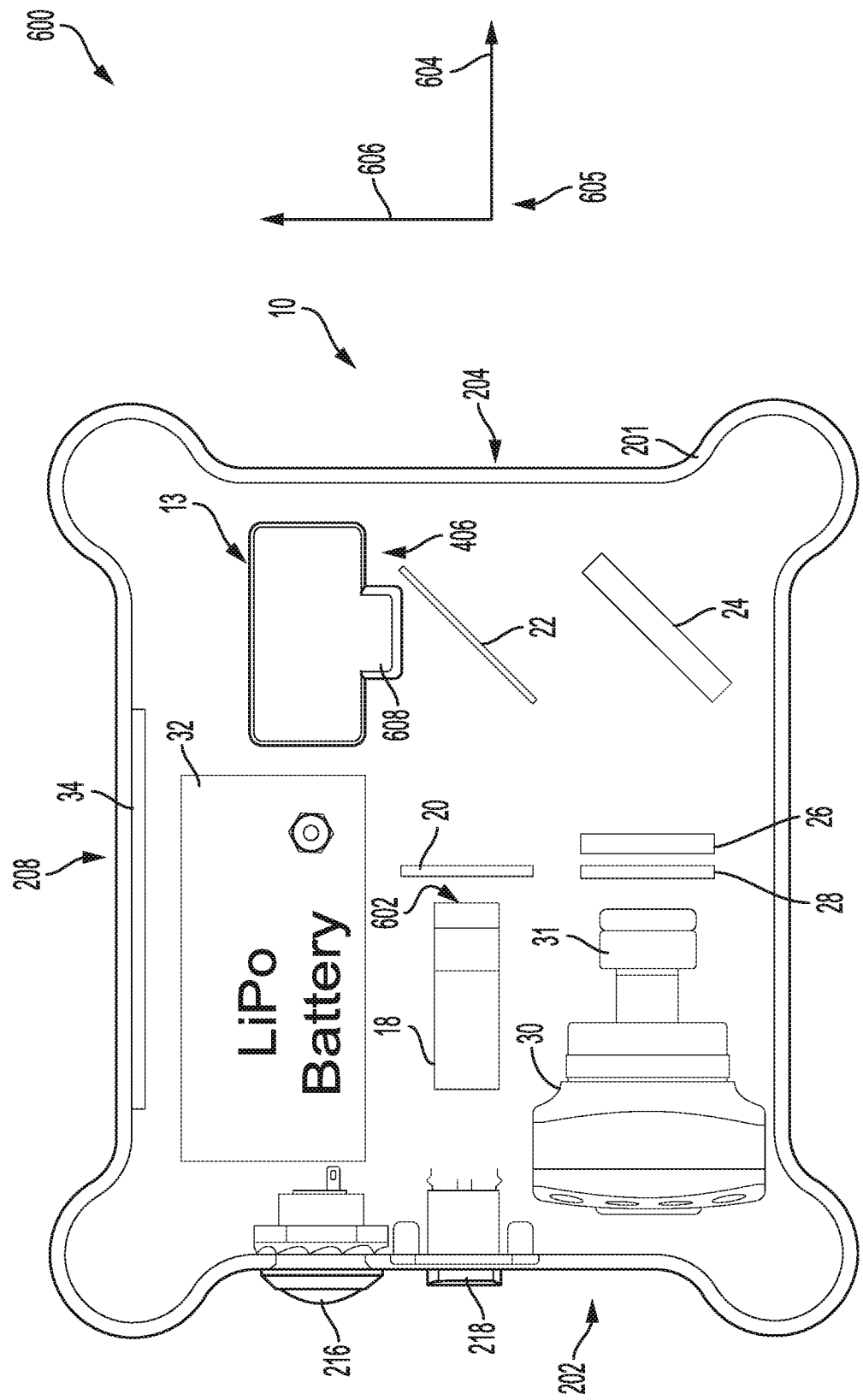
FIG. 6 shows a cross-sectional internal view of the portable biomolecule microarray assemblies of FIGS. 2 and 3.
Figure 7:
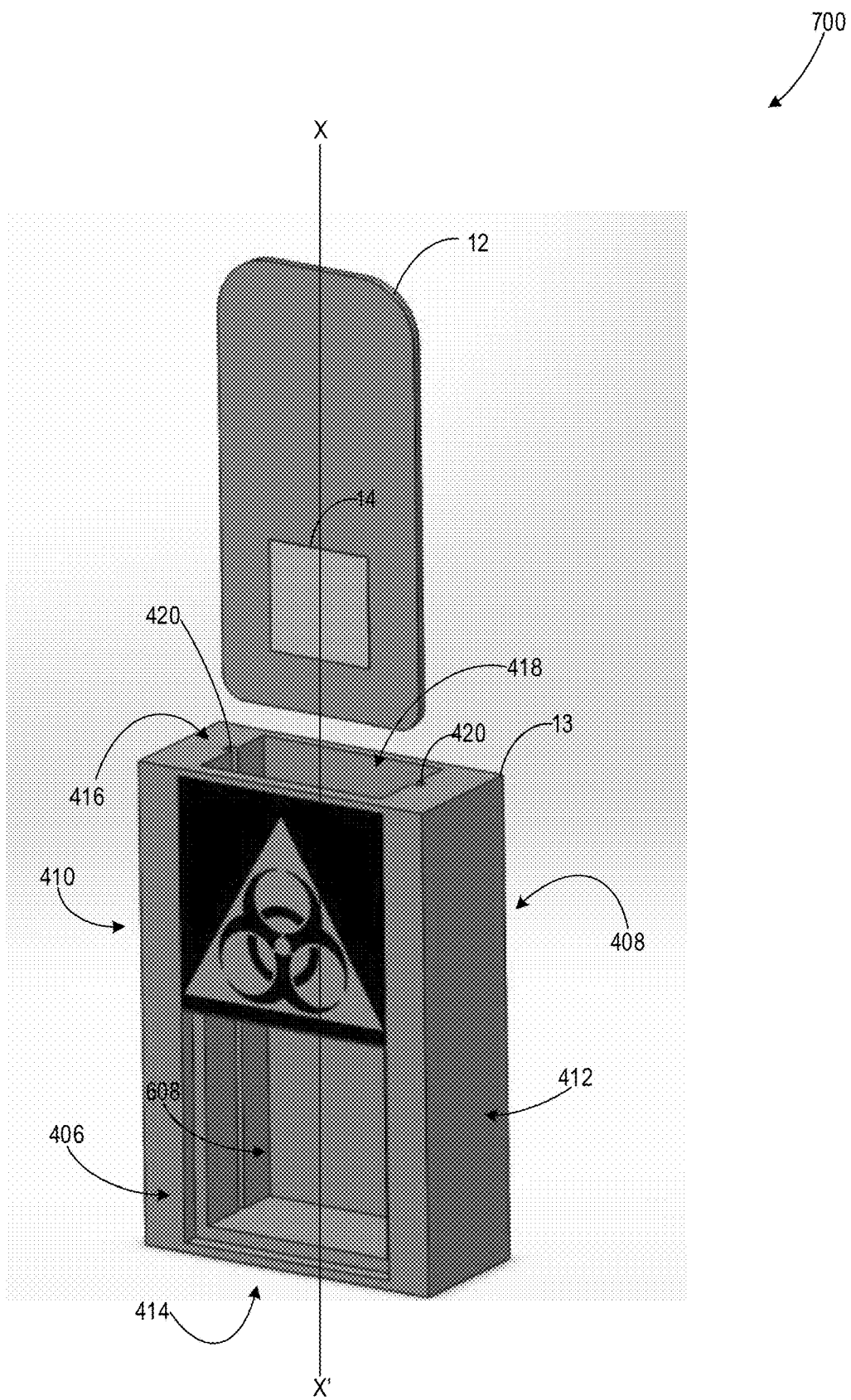
FIG. 7 shows a perspective view of an example microarray chip and cuvette which may be included in the portable biomolecule microarray assemblies of FIGS. 2 and 3.
Figure 8:
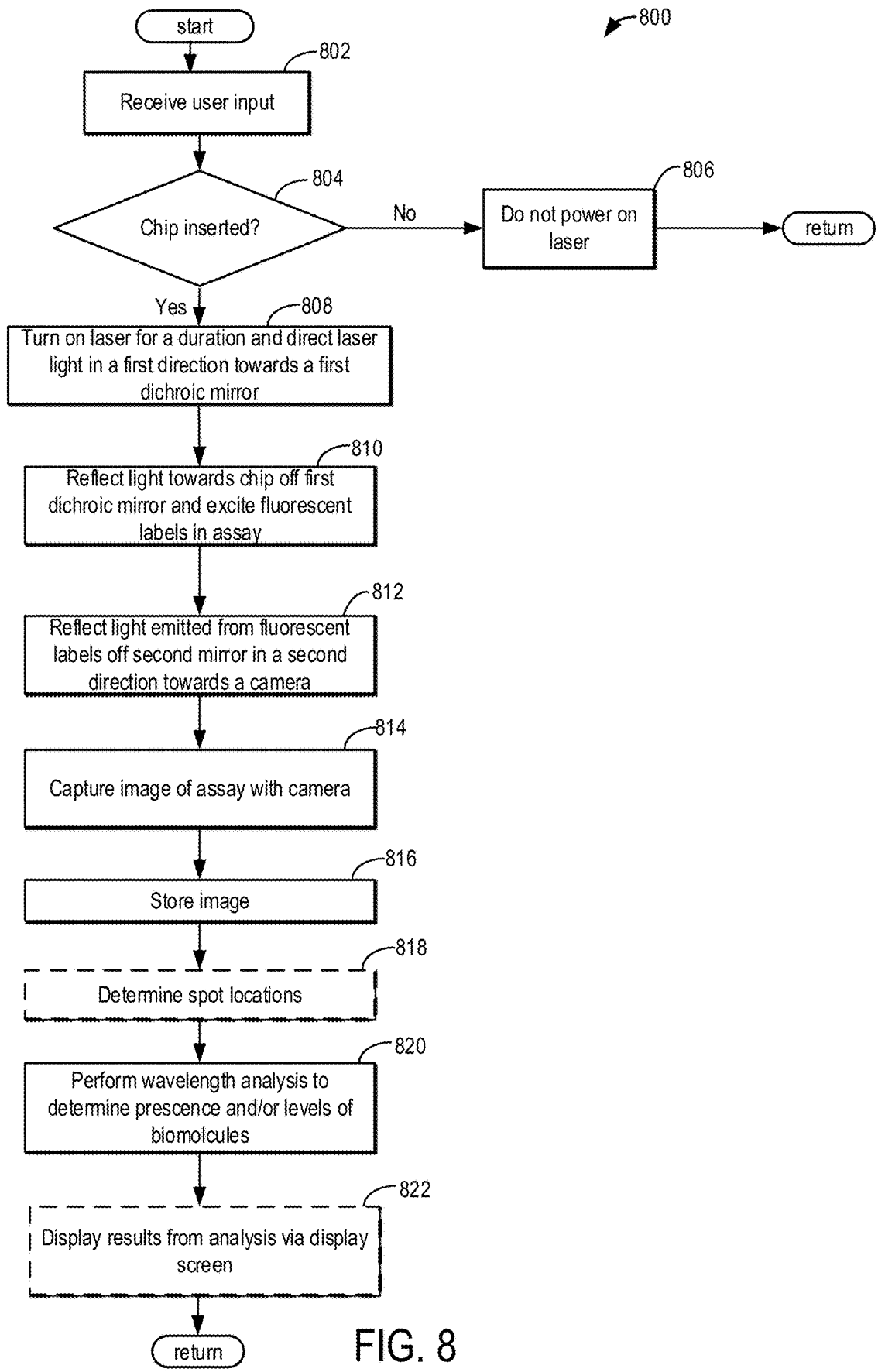
FIG. 8 shows a flow chart of an example method for imaging a biomolecule microarray assembly.

The following description relates to systems and methods for imaging and analyzing biomolecule microarrays. A biomolecule microarray assembly, such as the biomolecule microarray assembly shown in FIGS. 1-6, may be used to detect and estimate an amount of biomolecules, such as proteins, in a sample of lysate, blood, serum, tissue, cell cultures, etc. The biomolecule microarray assembly may include several components, as shown in FIGS. 1 and 6, such as a camera, laser, and dichroic mirrors for imaging the biomolecules. FIG. 8 shows an example method for imaging the biomolecules with the biomolecule microarray assembly. Biomolecules from the sample may be loaded onto a nitrocellulose coated microarray chip, an example of which is shown in FIGS. 4 and 7. The biomolecules may be labelled with one or more fluorescent tags to visualize biomolecule expression levels during imaging of the chip. In some examples, the microarray chip may be inserted into a chip cover or cuvette, such as the cuvette 13 shown in FIGS. 4 and 7, for preventing contamination of the sample.

Once the chip is inserted in the microarray assembly, light from a laser may be reflected via a first dichroic mirror onto the chip. In response to excitation from the laser beam, the fluorescent tags may emit light back towards the first dichroic mirror. The emitted light may then propagate through the first dichroic mirror and on to a second mirror, where the emitted light may be reflected to a camera for image acquisition. By including the second mirror in series with the first dichroic mirror, the camera and laser may be positioned parallel to one another, thereby reducing the size of the microarray assembly. As such, the portability of the microarray assembly may be increased relative to microarray assemblies with only one dichroic mirror.

Turning now to FIG. 1, it shows a schematic of a biomolecule analysis system 100. The biomolecule analysis system 100 may include a biomolecule microarray assembly 10 and a computer 122. In particular, FIG. 1 shows a two-dimensional schematic diagram showing components of the biomolecule analysis system 100 and how they may be electrically coupled to one another. As such, the actual sizes and relative positions of the components of the biomolecule microarray assembly 10 may be different than shown in FIG. 1. FIGS. 2-6, described further below, include three-dimensional schematics of the biomolecule microarray assembly 10, showing the relative sizes and positions of the components within the assembly 10. As such, the function of components of the biomolecule microarray assembly 10 may be described with reference to FIG. 1, while the positioning of each component within the assembly 10 may be described with reference to FIGS. 2-6.

In a preferred embodiment, the biomolecule microarray assembly 10 may be configured as a protein microarray for quantifying protein levels in one or more of lysate, whole blood, plasma, serum, saliva, CSF, or synthetic sample. As such, the biomolecule microarray assembly 10 may be used in the diagnosis and/or detection of infectious diseases. Specifically, antibody and/or antigen expression levels in a blood sample from a patient may be analyzed using the biomolecule microarray assembly 10 to identify a disease afflicting the patient. However, it should be appreciated that in other embodiments, the biomolecule microarray assembly 10 may be configured to image and analyze biomolecules other than proteins such as: DNA, cDNA, mRNA, siRNA, peptides, carbohydrates, lipids, whole cells, etc. Said another way, the biomolecule microarray assembly 10 may be any one of a protein, DNA, RNA, peptide, tissue, antibody, carbohydrate, lipid, or other microarray reader.

The biomolecule microarray assembly 10 may also be referred to herein as biomolecule microarray assay imager 10. The microarray assembly 10 may include a microarray chip 12, a portion or all of which may be coated with a nitrocellulose film 14, the nitrocellulose film 14 including a plurality of binding locations or wells 16 onto which a sample may be loaded. Thus, the binding locations 16 may be arranged on the nitrocellulose film 14 to form an array 15. The array 15 of wells 16 may chemically bind sample biomolecules of the sample to the chip 12. In the description herein, the wells 16 may also be referred to as spots 16 and/or binding locations 16. A sample may first be loaded onto the film 14 prior to insertion of the chip 12 into the microarray assembly 10 for imaging. The sample may in some examples comprise one or more of: blood, mucus, tears, sera, aqueous humor, or other bodily fluids that include antigens and/or antibodies of interest for infectious or non-infectious disease diagnosis. However, in other examples, the sample may include one or more of a tissue culture, cell culture, skin, hair, bone marrow, brain or other organs, feces or urine, and cerebral spinal fluid, for gene expression level quantification. Thus, the sample may include a plurality of biomolecules, of which only a subset may be desired for analysis. As such, target biomolecules, which comprise the subset of sample biomolecules desired for analysis, may be tagged with a fluorescent label. The fluorescent label may be any suitable fluorescent tag which may bind to the target biomolecules and emit light of a different wavelength than a light source in response to excitation from the light source, such as a laser. The array 15 of binding locations 16 may be referred to as an assay once the biomolecules from the sample have been chemically bound to the binding location 16, and have been tagged with the fluorescent label(s).

In some examples the fluorescent label may include Quantum Nanocrystal fluorescent-nanoparticles (QNC). QNCs are inorganic spheroidal particles that exhibit electronic quantum states confined to concentric layers of the materials that comprise the particle. QNCs may be composed from II/VI and II/V semiconductor alloys that are surface-functionalized to enhance bonding to bio-molecules such as biotin, proteins, and streptavidin. QNCs may have greater fluorescence brightness, optical stability and narrower emissions bands than organic dyes. However, in other examples, the fluorescent label may include other fluorophores or organic dyes such as food dye, ruthenium-based fluorescent dye, ethidium bromide, fluorescein, or green fluorescent protein (GFP). It should also be appreciated that multiple types of QNCs may be used for the fluorescent label, where each type of QNC may reflect a different wavelength of light. Thus, multiple types of QNCs that reflect different wavelengths of light may be utilized in the same assay 15.

Thus, the chip 12 may be removably coupled to the microarray assembly via a door (e.g., door 214 shown in FIGS. 2-5). The chip 12 may be relatively planar and may include a flat surface upon which the thin porous nitrocellulose film 14 is attached. The sample may be deposited onto the array 15 of target binding locations 16 included on the nitrocellulose film 14. The target binding locations 16 may each be configured to bind to one or more sample biomolecules in the sample. Thus, the target binding locations 16 may be configured to bind to one or more proteins, in examples where the microarray assembly 10 is a protein microarray. However, in other examples, the target binding locations 16 may be configured to bind to one or more oligonucleotides in examples where the microarray assembly 10 is a DNA microarray. The nitrocellulose film 14 may be sized to approximately a 12 mm by 12 mm square. However, in other examples the film 14 may be sized to be larger or smaller than 12 mm by 12 mm. Further, in other examples, the film 14, may be shaped differently than a square, such as circular, triangular, rectangular, etc. Thus, the chip 12 may be coated in a nitrocellulose film, which may be spotted with a plurality of target binding locations to form an array.

The target binding locations 16 may be approximately circular, and the diameter of the binding locations 16 may be in a range between 100-1000 microns. Further, the target binding locations 16 may be relatively evenly spaced from one another, where the spacing between target binding locations 16 may be in a range between 200 and 2000 microns. In some examples, the spacing of the target binding locations 16 may be based on the size of the target binding locations 16, where the spacing between target binding locations 16 may be approximately twice the diameter of the target binding locations 16. However, in other examples, the spacing may be greater or less than two times the diameter of the target binding locations 16. The film 14 may be configured to include approximately 1600 target binding locations 16. However, in other examples, the film 14 may include more or less than 1600 target binding locations 16.

In addition to the porous nitrocellulose, the binding locations 16 may include one or more binding molecules to which the biomolecules in the sample may bind. Thus, the binding molecules of the binding locations 16 may affix/immobilize the biomolecules to the target locations 16 on the chip 12. In examples where the microarray assembly 10 is configured as a protein microarray, the target binding locations 16 may comprise purified antigens, to which antibodies in the sample may bind. Thus, antigens may be spotted onto the nitrocellulose film 14, at the target binding locations 16. However, it should be appreciated that in other examples, the target binding locations 16 may comprise molecules other than antigens for binding to biomolecules of the sample other than antibodies. For examples, the target binding locations 16 may comprise antibodies, to which antigens in the sample may bind. In still further examples, the target binding locations 16 may comprise oligonucleotides or cDNA for binding to DNA or RNA in the sample. Alternatively, the target binding locations 16 may comprise only porous nitrocellulose, and may not include antigens or other binding molecules for binding to the sample biomolecules. In such examples, proteins in the sample may bind directly to the porous nitrocellulose at the target binding locations 16.

Additionally or alternatively, a reactive mixture of probe molecules including any of the suitable fluorescent labels, may be introduced to the sample biomolecules, once the sample biomolecules have adhered to the binding locations 16 on the chip 12. Specifically, the probe molecules may be configured to include QNC for fluorescently labelling the biomolecules in the spots 16. The probe molecules may be configured to selectively bind to the target biomolecules. In this way, only the target biomolecules may be tagged with the fluorescent labels. In examples where the sample includes antibodies and the microarray assembly 10 is configured as a protein microarray, probe molecules labeled with QNC, may be configured to selectively bind to only target antibodies in the sample. Said another way, the probe molecules labeled with QNC may be conjugated to the target antibodies in the sample. Thus, the probe molecules may be introduced to the binding locations 16 after the target antibodies have affixed to the binding locations 16 for fluorescently labeling the target antibodies.

To enable the mixing and binding of the biomolecules from the sample with the nitrocellulose film 14, an assay cover 17 may positioned over the nitrocellulose film 14. In some examples, the assay cover 17 may fully enclose the chip 12. However, in other examples, the assay cover 17 may only enclose the nitrocellulose film 14 and binding locations 16. One or more of the sample, a blocking solution, washing solution, and/or the reactive mixture may be mixed with the nitrocellulose film 14 in the assay cover 17. Further, the assay cover 17 may fluidically seal the nitrocellulose film 14 from the environment. Thus, the assay cover 17 may function as a container, holding various aqueous mixtures which may aid in binding the sample biomolecules to the binding locations 16, inhibiting binding of and/or removing sample biomolecules that are not the target biomolecules, and fluorescently tagging the target biomolecules. Put more simply, the assay cover 17 may permit reactions between the nitrocellulose film 14 and various aqueous mixtures during development of the assay.

Further, the assay cover 17 may serve to prevent contamination of the sample and film 14. By enclosing the film 14 in the assay cover 17, an amount of foreign materials such as dust, dirt, bacteria, enzymes, fungi, viruses, etc., that accumulate on the film 14 may be reduced. Specifically, the assay cover 17 may fluidically seal the film 14 from the outside environment prior to insertion of the chip 12 into the assembly 10.

Once the target biomolecules have been fluorescently tagged and chemically bound to the nitrocellulose film 14, the assay cover 17 may be removed from the chip 12, and the film 14 may be dried by flowing dry air over the surface of the chip 12. After the biomolecules in the sample have been bound to the nitrocellulose film 14 and fluorescently labeled, the chip 12 may be inserted into a cuvette 13.

The chip 12 may be inserted into the cuvette 13, and the cuvette 13 may fully enclose the chip 12 prior to insertion of the chip 12 in the microarray assembly 10. However, in other examples, the cuvette 13 may be inserted into the assembly 10 prior to insertion of the chip 12 into the cuvette 13, and the chip 12 may therefore be inserted into the cuvette 13 after the cuvette 13 has been inserted into the assembly 10. The structure of the cuvette 13 is described in greater detail below with reference to FIGS. 4 and 7. Cuvette 13 may serve a variety of purposes.

The cuvette 13 may fully enclose and/or hold the chip 12, and center the chip 12 within the assembly 10. Thus, the cuvette 13 may serve as a holder for the chip 12, which retains the chip 12 in a fixed position within the assembly 10 during imaging of the binding locations 16. In some examples, the assembly 10 may include one or more mechanical stabilizers 41 which may interface with external faces of the cuvette 13, for retaining the cuvette 13 in a fixed position within the assembly 10.

In some examples, the assay cover 17 may not be used to facilitate mixing of the sample and reactive mixture with the chip 12. In such examples, the cuvette 13 may provide the same above-mentioned functions as the assay cover 17. Thus, the cuvette 13 may in some examples function as a container, holding both the chip 12, and various aqueous mixtures which may aid in binding the sample biomolecules to the binding locations 16, inhibiting binding of and/or removing sample biomolecules that are not the target biomolecules, and fluorescently tagging the target biomolecules. Said another way, the cuvette 13 may permit reactions between the nitrocellulose film 14 and various aqueous mixtures during development of the assay.

Further, the cuvette 13 may serve to prevent contamination of the chip 12. By fully enclosing the chip 12 in the cuvette 13, an amount of foreign materials such as dust, dirt, bacteria, enzymes, fungi, viruses, etc., that accumulate on the chip 12 may be reduced. Specifically, as shown below with reference to FIGS. 4 and 7, the cuvette 13 may fluidically seal the chip 12 from the outside environment, once the chip 12 is inserted into the cuvette 13.

The chip 12 may be inserted into the microarray assembly 10 for imaging of the binding location 16. Specifically, in some examples where the cuvette 13 is not included in the assembly 10, the chip 12 may be inserted directly into the microarray assembly 10. However, in other examples where the cuvette 13 is included in the microarray assembly 10, the cuvette 13 including the chip 12 may be inserted into the microarray assembly 10. The cuvette 13 may include an authentication device which may be either mechanical or electronic, which may engage with the microarray assembly 10 when the cuvette 13 is inserted. The authentication device may ensure that the array 15 is imaged only when the cuvette 13 is inserted in the microarray assembly 10.

Once the chip 12 is inserted into the microarray assembly 10, the array 15 may be imaged by the microarray assembly 10 to visualize biomolecule expression levels. Imaging of the array 15, may include exciting the fluorescent labels via a laser 18, and capturing the light emitted from the fluorescent labels with a camera 30. The laser 18 may be a violet diode laser, and may emit a light beam in a range of wavelengths between 400 and 450 nanometers. Light emitted from the laser 18 may travel in a first direction towards a first dichroic mirror 22, as shown by light propagation arrow 19*a* in FIG. 1. Before reaching the first dichroic mirror 22, light from the laser 18 may first pass through a diffusing element 20 positioned between the first dichroic mirror 20 and the laser 18. The diffusing element 20 may be positioned approximately perpendicular to the direction of light propagation from the laser 18 to increase uniformity of the beam profile of the light from the laser 18. Thus, by including the diffusing element 20 the uniformity of light intensity across the surface area of the array 15 may be increased. Said another way, the intensity of light received by each binding location 16 may be relatively the same after passing the laser light through the diffusing element.

Upon reaching the first dichroic mirror 22, light from the laser 18 may be reflected by approximately 90 degrees, and may propagate toward the chip 12 in a second direction as shown by the light propagation arrow 19*b* in FIG. 1. Thus, the first dichroic mirror 22 may be configured to reflect light from the laser, while allowing other wavelengths of light to pass through. As such, the first dichroic mirror 22 may only reflect light of wavelengths between a first range of 400 and 450 nm. Said another way, the first dichroic mirror 22 may be selectively transparent to light of wavelengths longer than 450 nm. Thus, only light with a wavelength greater than 450 nm may pass through the first dichroic mirror 22 without being reflected. Further, the first dichroic mirror 22 may be positioned at approximately a 45 degree angle with respect to the laser 18, so that light emitted from the laser 18 is deflected approximately 90 degrees towards the chip 12. More specifically, a first surface 21 of the first dichroic mirror 22 which faces the laser 18, may be orientated at approximately a 45 degree angle with respect to the first direction of light propagation. Thus, the first dichroic mirror 22 and second mirror 24 may be orientated to that their first surfaces 21 and 25, respectively are orientated at a 45 degree angle with respect to a light source end 602 of the laser 18 from which a laser beam is emitted. Said another way, the laser 18 may be pointed at the first dichroic mirror 22 so that light from the laser 18 may reach the mirror 22 at an incident angle of approximately 45 degrees. However, in other examples, the mirror 22 may be angled with respect to the laser 18 at an angle greater or less than 45 degrees. Further, the first dichroic mirror 22 and second mirror 24 may be orientated to that their first surfaces 21 and 25, respectively, are orientated at a 45 degree angle with respect to the lens 31 of the camera 30. Additionally or alternatively, the first dichroic mirror 22 and second mirror 24 may be orientated to that their first surfaces 21 and 25, respectively, are orientated at a 45 degree angle with respect to the front wall 406 and optically clear window 608 of the cuvette 13.

Light from the laser 18 may reach the chip 12, and excite the fluorescent labels (e.g., QNC). Said another way, when exposed to light from the laser 18, the fluorescent labels chemically bound to the target biomolecules may emit light back towards the first dichroic mirror 22 in a third direction which may be approximately opposite the second direction as shown by fluorescent emission light arrows 23*a*. Light emitted from the laser is shown by the solid arrows 19*a* and 19*b*, while light emitted from the array 15 is shown by dashed arrows 23*a* and 23*b*. Emission light from the fluorescent labels of the array 15 may be of a different wavelength than the light from the laser 18. Specifically, the wavelength of the emission light may be greater than the wavelength of the light emitted from the laser 18. In some examples the wavelength of the emission light from the array 15 may be in a range between 500 and 900 nm.

As described above, the first dichroic mirror 22 may only reflect light emitted from the laser 18. Thus, since the light emitted from the fluorescent labels of the array 15 may be greater than that from the laser 18, the light emitted from the fluorescent labels may pass relatively unobstructed through the first dichroic mirror 22 and on to a second mirror 24. Thus, as shown in FIG. 1, the array 15, first dichroic mirror 22, and second mirror 24 may be relatively aligned with one another along a straight line, with the first dichroic mirror 22 being positioned between the second mirror 24 and the array 15. However, light emitted from the array 15 may be reflected off a first surface 25 of the second mirror 22. Thus, the second mirror 24 and first dichroic mirror 22 may reflect different wavelengths of light. Specifically, the second mirror 24 may reflect a second range of wavelengths of light that is greater than the first range of wavelengths reflected by the first dichroic mirror 22. In some examples, the second mirror 24 may reflect substantially all wavelengths of light. Thus, the first dichroic mirror 22 may be configured to reflect electromagnetic waves only with wavelengths up to 450 nm, whereas the second mirror 24 may be configured to reflect electromagnetic waves up to 1000 nm. Additionally, in some examples, the second mirror 24 may not reflect light with wavelengths less than 450 nm. In this way, light from the laser 18 may be reflected by the first dichroic mirror 22, and light emitted from the array 15 may pass through the first dichroic mirror 22 without being reflected. However, the second mirror 22 may be configured to reflect light emitted from the array 15, and as such, upon reaching the first surface 25 of the second mirror 22, light emitted from the array 15 may be reflected approximately 90 degrees towards the camera 30.

Thus, the second mirror 24 may be orientated at approximately a 45 degree angle with respect to the array 15, in the same or similar orientation as the first dichroic mirror 22. Thus, the second mirror 24 and the first dichroic mirror 22 may be orientated substantially parallel to one another. In this way, incident light from the array 15 may be reflected off the first surface 25 of the second mirror 24 in a fourth direction, substantially parallel and opposite the first direction as shown by fluorescent emission light arrows 23*b*. Thus light reflected off the second mirror 24 may propagate substantially parallel to and opposite the direction of propagation of light emitted from the laser 18.

Camera 30 may therefore be aligned approximately parallel to the laser 18. Said another way, the camera 30 and laser 18 may be positioned on the same side of the first dichroic mirror 22 and the second mirror 24. By including the second mirror 24, and positioning the camera 30 parallel to the laser 18, the compactness of the microarray assembly may be increased, and therefore the size of the microarray assembly 10 may be reduced. In this way, the laser 18 may emit light in a first direction towards the first dichroic mirror 22, and the camera 18 may receive light emitted from the array 15 in a fourth direction, the fourth direction opposite the first direction. The camera 30 may therefore by orientated so that a lens 31 of the camera 30 faces the second mirror 24. Specifically, the lens 31 may face the first surface 25 of the second mirror 24 at approximately a 45 degree angle.

Thus, the camera 30 may be orientated parallel with respect to the laser 18 so that the lens 31 faces the same direction as the source of light from the laser 18. In some examples, the camera 30 and laser 18 may be positioned adjacent to one another such that no additional components separate the laser 18 and camera 30. However, in other examples the camera 30 and laser 18 may be spaced away from one another. In this way, the parallel arrangement of the laser 18 and camera 30 may be referred to herein as an optically folded configuration or arrangement since the light emitted by the laser 18, and the light received by the camera 30 propagate in approximately parallel but opposite directions. Said another way, the camera 30, laser 18, first dichroic mirror 22, and second mirror 24 may positioned in an optically folded arrangement, so that light emitted from the laser propagates in a parallel and opposite direction to light reflected towards the camera from the second mirror.

Before reaching the camera 30, light emitted from the array 15 and reflected off the second mirror 24, may pass through one or more filters. In one example, a bandpass filter 26 may be positioned between the camera 30 and the second mirror 24. Additionally or alternatively a longpass filter 28 may be positioned between the camera 30 and the second mirror 24. In examples where both the longpass filter 28 and the bandpass filter 26 are included in the assembly 10, the bandpass filter 26 may be positioned more proximate the second mirror 24 than the longpass filter 28. Together, the longpass filter 28 and the bandpass filter 26 may only be optically clear to a desired range of wavelengths of electromagnetic waves. In this way, only light in the wavelength range of that emitted from the fluorescent labels may pass through the filters 28 and 26 en route to the camera 30. As one example, only light with a wavelength of less than 800 nm may pass through the filters 28 and 26. Thus, by including the filters 26 and 28, background noise (e.g., light emitted from the array 15 not from the fluorescent labels) may be significantly reduced as compared to microarray assemblies not including the filters.

Additionally, in some examples, the filters may be selectable. Thus, the assembly 10 may be adaptable to multi-color multiplexing detection of several fluorescent labels by providing multiple filters that may be selectable to filter different wavelengths of light based on the desired fluorescent label. As such, the camera 30 may be configured to independently detect two or more signals from multiple fluorescent labels of different colors.

Although in the preferred embodiment of the microarray assembly 10 described above, second mirror 24 is included in the assembly 10, it should also be appreciated that in other embodiments, the microarray assembly 10 may not include second mirror 24. In such embodiments where second mirror 24 is not included in the assembly 10, the camera 30 may be positioned so that the lens 31 directly faces the array 15. Said another way, the lens 31 may be positioned perpendicular to the direction of light propagation from the array 15, so that light emitted from the array 15 may pass through the lens 31 and be captured in an image by the camera 30. Thus, the camera 30 may be positioned perpendicular to the laser 18, so that light emitted from the array 15 may be received and imaged by the camera 30, after the light passes through the first dichroic mirror 22. Therefore, in examples where mirror 24 is not included in the assembly, light emitted by the array 15 may pass in a relatively straight line to the lens 31 of the camera, and may not be reflected by any mirror en route to the camera 30. Further, the filters 26 and 28 may be positioned between the first dichroic mirror 22 and the lens 31 of the camera 30 in examples where the camera 30 is positioned perpendicular to the laser 18 and second mirror 24 is not included in the assembly 10. Thus, the filters 26 and 28, lens 31, and camera 30, may be aligned antiparallel to emission light arrows 23*a* for capturing light emitted from the array 15. Said another way, array 15, first dichroic mirror 22, filters 26 and 28, lens 31, and camera 30 may all be aligned with one another in a substantially straight line perpendicular to the first direction shown by light propagation arrows 19*a*.

In this way, the lens 31 may gather light produced from the fluorescent labels, and the camera 30 may capture an image of the array 15. The camera 30 may be a digital camera, configured to acquire digital images of the array 15 and the spots 16 positioned therein. Specifically, light emitted from the array 15 in response to excitation from the laser 18 may be captured by the camera 30. The resolution of the image of the array 15 may depend on the distance of the camera 30 from the array 15, the focal length of the lens 31, the magnification of the camera 30, and the surface area of the array 15. In some examples, the camera 30 may be a 5 megapixel camera. However, in another example, the camera 30 may be a 3 megapixel camera. In still further examples, the megapixel of the camera 30 may be a range between 2 and 7 megapixels. The focal length of the lens 31 may be one of 30, 25, 17.5, or 12 mm. However, in other examples the focal length of the lens 31 may be a range between 5 and 30 mm. A width of the array 15 may in some examples be 25 mm. However, in other examples, the array 15 may have a width of 12.5 mm. In still further examples, the width of the array may be approximately 6.25 mm. Further, the width of the array 15 may be a range between 5 and 30 mm. The optical path length between the array 15 and the camera 30 may be approximately 120 mm. However, in other examples, the optical path length between the array 15 and the camera 30 may be greater or less than 120 mm. Thus, the resolution of the images captured by the camera 30 may be in a range between 2 and 10 microns. Specifically, by reducing the size of the array 15 to a width of approximately 12.5 mm, and configuring the camera 30 with a magnification of 0.45 and lens focal length of 25 mm, the resolution of the image may be improved to 4.9 microns.

Images captured by the camera 30, may in some examples be transferred to a computer 122 for analyzation thereof. Computer 122 may be any computing device configured to access a network including but not limited to a server, personal computer, laptop, a smartphone, a tablet, and the like. In some examples, the microarray assembly 10 may be electrically coupled to the computer 122 via a wired connection such as a USB port.

Computer 122 may include a logic subsystem 123 and a data-holding subsystem 124. Computer 122 may additionally include a display subsystem 125, communication subsystem 126, and/or other components not shown in FIG. 1. For example, computer 122 may also optionally include user input devices such as keyboards, mice, game controllers, cameras, microphones, and/or touch screens.

Logic subsystem 123 may include one or more physical devices configured to execute one or more instructions. For example, logic subsystem 123 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

Logic subsystem 123 may include one or more processors that are configured to execute software instructions. Additionally or alternatively, the logic subsystem 123 may include one or more hardware or firmware logic machines configured to execute hardware or firmware instructions. Processors of the logic subsystem 123 may be single or multi-core, and the programs executed thereon may be configured for parallel or distributed processing. The logic subsystem 123 may optionally include individual components that are distributed throughout two or more devices, which may be remotely located and/or configured for coordinated processing. One or more aspects of the logic subsystem 123 may be virtualized and executed by remotely accessible networking computing devices configured in a cloud computing configuration.

Data-holding subsystem 124 may include one or more physical, non-transitory devices configured to hold data and/or instructions executable by the logic subsystem 123 to implement the herein described methods and processes. When such methods and processes are implemented, the state of data-holding subsystem 124 may be transformed (for example, to hold different data). For example, the data holding subsystem 124 may be configured to store images from the camera 30. The images may be modified, and/or analyzed based on instructions stored in the logic sub system 123.

Data-holding subsystem 124 may include removable media and/or built-in devices. Data-holding subsystem 124 may include optical memory (for example, CD, DVD, HD-DVD, Blu-Ray Disc, etc.), and/or magnetic memory devices (for example, hard drive disk, floppy disk drive, tape drive, MRAM, etc.), and the like. Data-holding subsystem 124 may include devices with one or more of the following characteristics: volatile, nonvolatile, dynamic, static, read/write, read-only, random access, sequential access, location addressable, file addressable, and content addressable. In some embodiments, logic subsystem 123 and data-holding subsystem 124 may be integrated into one or more common devices, such as an application-specific integrated circuit or a system on a chip. Together, the logic subsystem 123 and data-holding subsystem 124 may be configured to store images captured from the camera 30, and analyze the images to determine biomolecule expression levels in each of the target binding location 16 of the array 15.

Thus, the logic subsystem 123 may include one or more algorithms for processing and analyzing data received from the camera 30. Thus, in order to compare the intensity of different wavelengths of light emitted from the different binding locations 16, the logic subsystem 123 may include one or more algorithms or software for image analyzation. One or more of a combination of different algorithms for data normalization and statistical techniques, such as artificial neural networks, multivariate statistics and tree algorithms may be stored in the logic subsystem 123 for analyzing the images captured by the camera 30 to detect for and/or quantify biomolecule expression levels in the sample based on relative intensities of different wavelengths of light. In this way, in examples where the microarray assembly 10 is configured as a protein microarray, light received from the binding locations 16 and captured by the camera 30 may be compared and analyzed to detect for biomarkers of infectious diseases. However, it should be appreciated that the images may be analyzed to detect for and/or quantify gene expression levels, oligonucleotides, antibodies, antigens, etc.

When included, display subsystem 125 may be used to present a visual representation of data held by data-holding subsystem 124. As the herein described methods and processes change the data held by the data-holding subsystem 124, and thus transform the state of the data-holding subsystem 124, the state of display subsystem 125 may likewise be transformed to visually represent changes in the underlying data. For example, the images captured by the camera 30 may be displayed to a user via the display subsystem 125. Further, modifications to and/or analysis of the images may be displayed to the user via the display subsystem 125. Display subsystem 125 may include one or more display devices utilizing virtually any type of technology. Such display devices may be combined with logic subsystem 123 and/or data-holding subsystem 124 in a shared enclosure, or such display devices may be peripheral display devices.

When included, communication subsystem 126 may be configured to communicatively couple user device 122 with one or more other computing devices, such as controller 34 of the microarray assembly 10. Thus, in some examples, the microarray assembly 10 may be electrically coupled to the computer 122 by a wired connection as shown by the dotted line in FIG. 1. However, in other examples, the microarray assembly 10 may be wirelessly coupled to the computer 122 via any suitable wireless connection for data transfer such as Wifi or Bluetooth. Thus images taken from the camera 30 may be transferred to the computer 122 via either a wired electrical connection and/or a wireless connection. However, in other examples, the microarray assembly 10 may include a memory chip 33 which may be removably coupled to assembly 10 for storing images captured by the camera

10. The memory chip 33 may be any suitable memory storage device such as a USB memory stick, SD card, micro-SD card, etc. Images may be transferred from the memory chip 33 onto the computer 122 by removing the memory chip 33 from the microarray assembly, and inserting the memory chip 33 into the computer 122.

Communication subsystem 126 may include wired and/or wireless communication devices compatible with one or more different communication protocols. As non-limiting examples, communication subsystem 126 may be configured for communication via a wireless telephone network, a wireless local area network, a wired local area network, a wireless wide area network, a wired wide area network, etc. In some embodiments, communication subsystem 126 may allow computer 122 to send and/or receive messages to and/or from other devices, controller 34, via a network such as the public Internet.

Although images from the camera 30 may be transferred to the computer 122 for analysis, it should be appreciated that in other embodiments, the microarray assembly 10 may perform image analysis on its own. For example, the controller 34 of the microarray assembly 10 may include computer readable instructions for analysis of the images captured by the camera 30. Thus, the controller 34 may be configured and may function the same or similar as the logic subsystem 123 and data-holding subsystem 124 of the computer 122 described above. Said another way, logic subsystem 123 and data-holding subsystem 124 may be included in the controller 34 of the microarray assembly 10 for processing and analyzation of the images captured by the camera 30. In such examples, the microarray assembly 10 may not be electrically coupled to the computer 122. Further, in examples where image analysis is performed by the microarray assembly 10, the microarray assembly may further include a display (shown below with reference to FIG. 3) such as display subsystem 125.

Controller 34 may be configured to operate one or more of the laser 18 and camera 30 for capturing images of the array 15. In some examples, the controller 34 may be configured to receive input from a user via either the computer 122 or a display screen or button pad located on the microarray assembly 10. Thus, a user may send signals to the controller 34 via either the computer 122 or through a display screen or button pad located on the microarray assembly 10. Based on signals received from the user, the controller 34 may send signals to the laser 18 for emitting light, and/or to the camera 30 for capturing an image of the array 15.

Power to the controller 34, laser 18, and camera 30 may be provided by the computer 122 in examples where the microarray assembly 10 is coupled to the computer 122 via a wired connection. However, in other examples, the microarray assembly 10 may include its own battery 32 for powering the various components of the microarray assembly 10. The battery 32 may be any suitable battery such as lithium-ion, lead-acid, solid polymer electrolyte, molten salt, etc. The battery 32 may be a rechargeable battery, and may be charged by a wired electrical connection to computer 122, or other electrical source such as an electrical socket. The battery 32 may provide electrical power to the laser 18, where the current of said electrical power may be any current level within a range of currents between 1-2 amps. In still further examples, the microarray assembly 10 may include its own power cord for receiving power from an electrical socket.

Although in the example of FIG. 1, microarray assembly 10 is described as being capable of imaging and/or analyzing microarray assays, it should also be appreciated that other types of assays may be imaged and/or analyzed using the microarray assembly 10. For example, the microarray assembly 10 may be configured to image and/or analyze colorimetric assays. In such examples, the microarray assembly 10 may include a white light source in place of laser 18. Thus, a source of white light may be used to illuminate the array 15 instead of the laser 18. Further, the first dichroic mirror 22 may be replaced with a beam splitter capable of reflecting only a portion of the white light incident on it from the white light source to the array 15. The orientation and position of the white light source within the assembly 10 may be the same or similar to the laser 18. Similarly, the orientation and position of the beam splitter may be the same or similar to first dichroic mirror 22. In this way, white light from the white light source may be reflected onto the array 15 by the beam splitter. Based on the chromophores of the biomolecules in the assay, the biomolecules may absorb certain wavelengths of the white light, while reflecting others.

The colors reflected by the chromophores may determine the wavelengths of light captured in the image of the array by the camera 30. The colors captured by the camera may also be adjusted by various filters, such as filters 26 and 28. For example, one or more filters may be utilized to exclude certain wavelengths of light reflected from the array, and may only allow a desired range of wavelengths to pass through to the camera 30 for image acquisition. En route to the filters, at least a portion of the light reflected from the array 15 may pass through the beam splitter, and on to the second mirror 24, since the beam splitter may only reflect a portion of incident light, and may allow the remaining portion of incident light not reflected, to pass there-through. In this way, by allowing light to be both reflected and transmitted, the beam splitter may serve to reflect at least a portion of the white light emitted by the white light source to the array 15, for illuminating the biomolecules in the assay. Additionally, the beam splitter may serve to allow at least a portion of the light reflected by the array 15, to pass through the beam splitter and on to the filters and camera 30 for imaging of the array 15.

Turning now to FIGS. 2-6 they show schematics of the biomolecule microarray assembly 10 which may be used to image and visualize the presence and/or amount of biomolecules in a sample collected on the microarray chip 12. FIGS. 2-6 show three-dimensional schematics of the microarray assembly 10. Further, the relative sizes and positions of the components included in the microarray assembly 10 are shown in FIGS. 2-6. Thus, FIGS. 2-6 may be drawn approximately to scale. However, it should be appreciated that in other examples, the relative sizing and positioning of components in the microarray assembly 10 may be different than depicted in FIGS. 2-6. Since FIGS. 2-6 all show schematics of the microarray assembly 10, the FIGS. 2-6 may be described together in the description herein. Thus, components of the microarray assembly 10 introduced in the description of any one of FIGS. 2-6, may not be reintroduced or described again. Further components of the microarray assembly 10 already introduced in FIG. 1 may not be discussed again in the description of FIGS. 2-6 herein.

Figure 2:
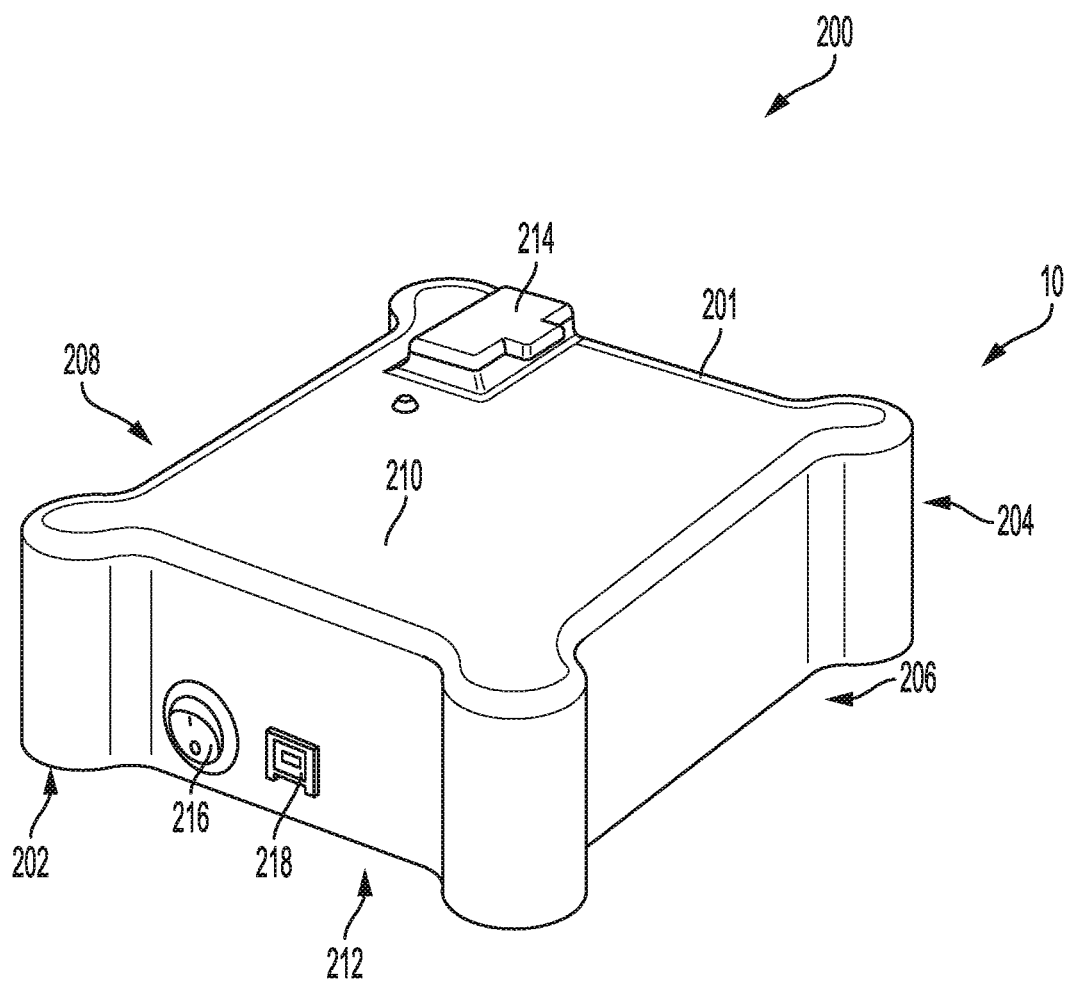
FIG. 2 shows a perspective view of a first embodiment of a portable biomolecule microarray assembly.
Figure 3:
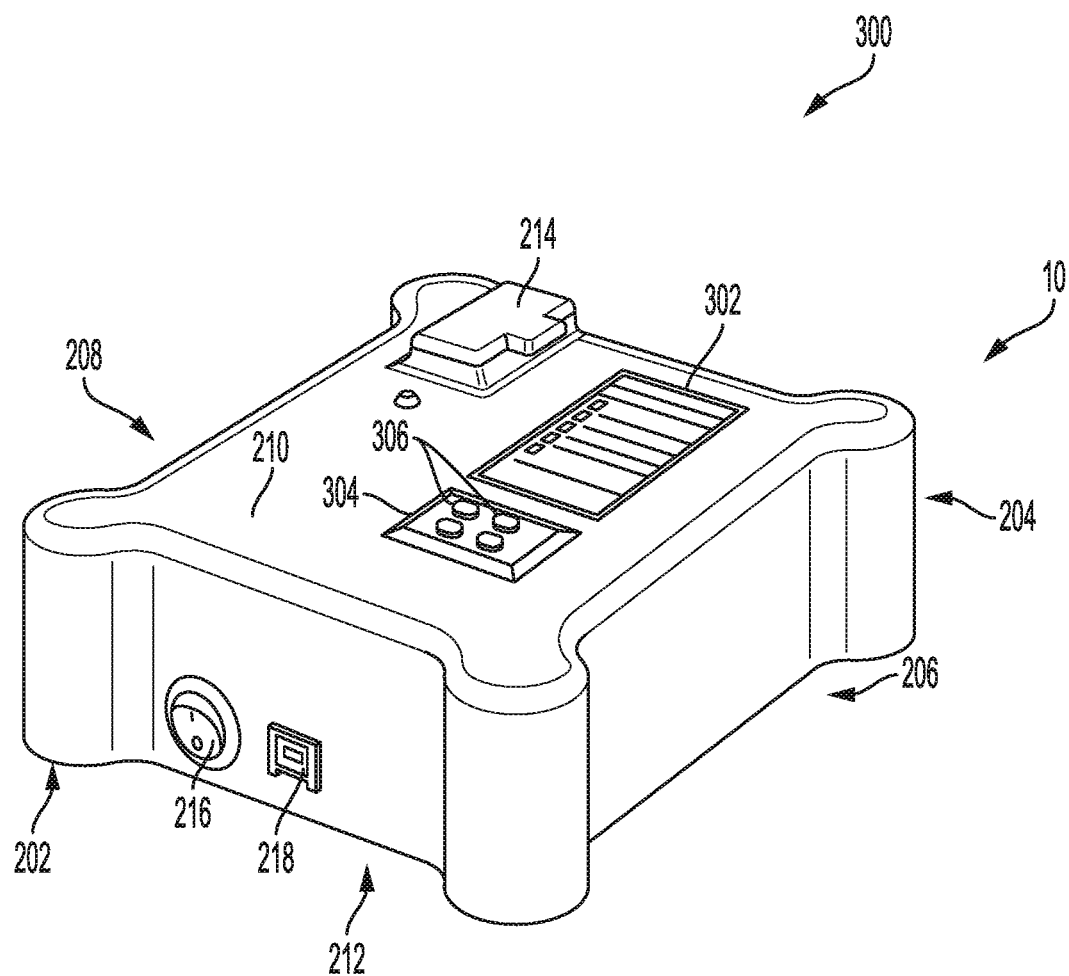
FIG. 3 shows a perspective view of a second embodiment of the portable biomolecule microarray assembly of FIG. 2.
Figure 4:
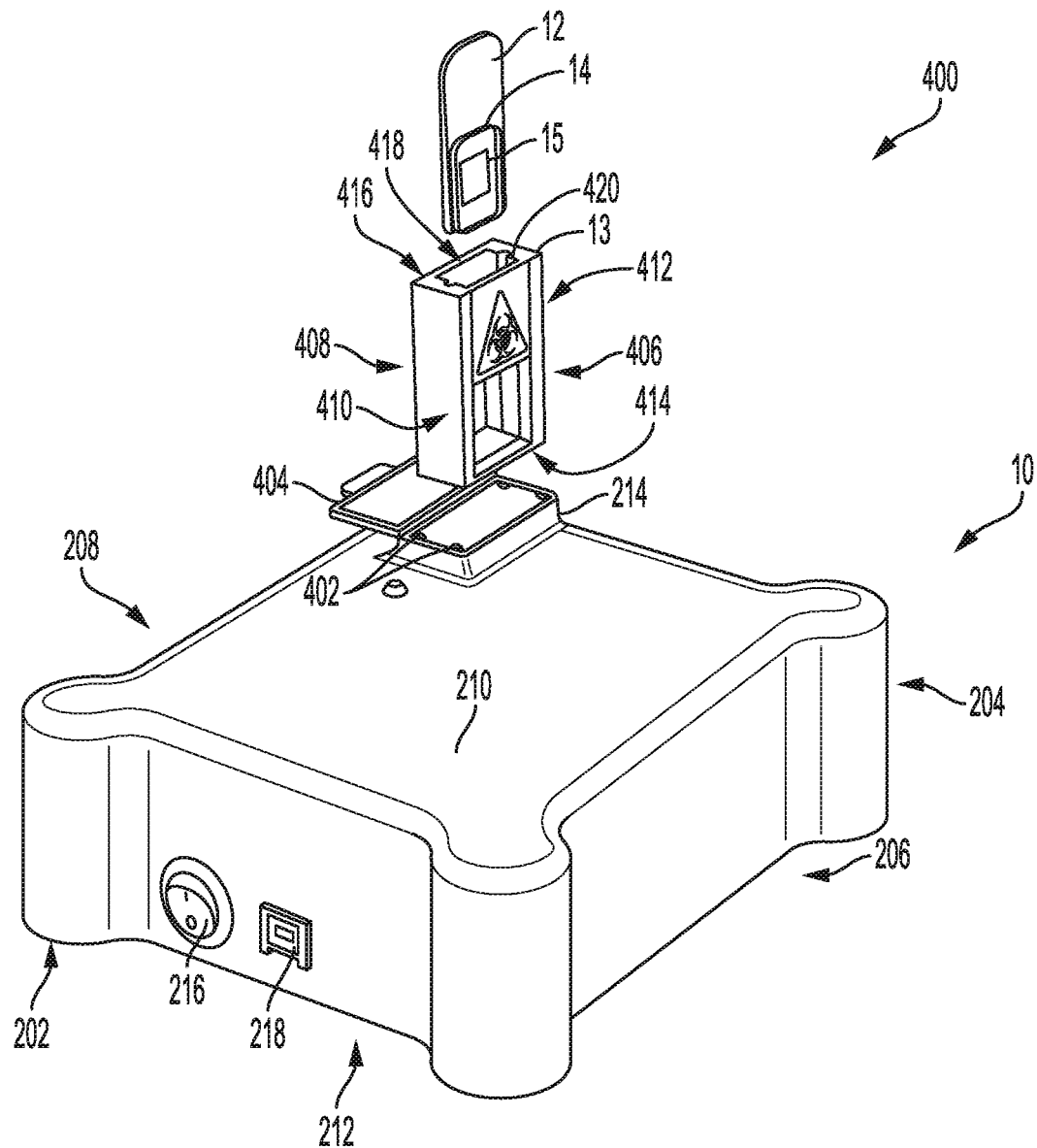
FIG. 4 shows an exploded view of the portable biomolecule microarray assembly of FIG. 2 including a microarray chip.

The microarray assembly 10, as shown in FIGS. 2-6, may comprise six or more walls, defining a housing 201 of the microarray assembly 10. Each of the walls may include an interior face (proximate to interior components of the microarray assembly 10) and an exterior (or outside) face, the exterior face visible to a user. Specifically, the microarray assembly 10 may comprise a front wall 202 with a front exterior face opposite from a back wall 204. Further, the assembly 10 may comprise a first side wall 206 opposite from a second side wall 208, and a top wall (e.g., top face or surface) 110 opposite from a bottom wall (e.g., bottom face or surface) 212. The top wall 210 may comprise multiple components such as a door 214 for receiving the microarray chip 12 containing the sample to be analyzed. Further, in some examples as shown in FIG. 3 the top wall 110 may include a display screen 302 and/or a button pad 304 for receiving input from a user and/or for providing feedback to the user.

Focusing now on FIG. 2, it shows an exterior perspective view 200 of a first embodiment of the microarray assembly 10 shown above in FIG. 1. Specifically, the perspective view 200 and shown in FIG. 2, may be an axonometric projection of the microarray assembly 10, showing the assembly 10 as viewed from a skew direction in order to reveal more than one side of the assembly 10. Further, it should be appreciated that all perspective views of the assembly 10 shown herein (e.g., perspective views 300, 400, and 500 shown below with reference to FIGS. 3, 4, and 5, respectively) may also be axonometric projections of the microarray assembly 10. In the embodiment shown in FIG. 2, the microarray assembly 10 may be configured as an image capturing device only. Thus, the microarray assembly 10 as shown in FIG. 1 may be configured to capture images of the array 15 (not shown in FIG. 2), and may not be configured to analyze the images.

The microarray assembly 10 may be shaped as a rectangular prism as shown in FIG. 1. However, it should be appreciated that other shapes and/or sizes of the microarray assembly 10 are possible. The microarray assembly 10 may include a door 214 positioned on the top wall 110 for receiving the chip 12 and/or cuvette 13 (not shown in FIG. 2). Further, the microarray assembly 10 may include a USB port 216 and/or a power switch 218 on the front wall 202. However, it should be appreciated that one or more of the USB port 216 and power switch 218 could be located at other positions on the microarray assembly 10 such as on any of the other walls 204, 206, 208, 210, and 212. The USB port 216 may be configured to electrically couple the microarray assembly 10 to a computer (e.g., computer 122 shown in FIG. 1) for transferring images captured by the camera (not shown in FIG. 2) to the computer for analysis thereof. Additionally, the microarray assembly 10 may draw power from the computer or a wall socket through the USB port 216. Thus, the battery 32 may be charged through a wired electrical connection provided by the USB port 216 to any suitable power source such as the computer, electrical socket, vehicle power outlet, etc. Further, the power switch 218 may be adjusted by a user to power on and power off the microarray assembly 10. The power switch 218 may be any suitable digital or mechanical two-way switch.

Moving on to FIG. 3, it shows an exterior perspective view 300 of a second embodiment of the microarray assembly 10 including a display screen 302 and/or button pad 304. Specifically, in the embodiment shown in FIG. 3, the microarray assembly 10 may be configured to both capture and analyze images taken of the array 15 (not shown in FIG. 3). Thus, in the example shown in FIG. 3, the microarray assembly 10 may be configured to display results from an analysis of the array 15 (shown above in FIG. 1) via the display screen, where the results may include identification and/or detection of a disease, antibody expression levels, biomolecule expression levels, gene quantification, etc. As such, the microarray assembly 10 in the example of FIG. 3 may provide an infectious disease diagnosis.

In order to receive input from a user, and display results from the image analysis to the user, the microarray assembly 10 may include the display screen 302 and/or button pad 304. As shown in the example of FIG. 3, the display screen 302 and/or button pad 304 may be positioned on the top wall 210 of the microarray assembly 10. However, it should be appreciated that in other examples, the display screen 302 and/or button pad 304 may be positioned elsewhere on the assembly 10, such as any of the other walls 202, 204, 206, 208, and 212. The display screen 302 may be any suitable display screen such as an LCD, CRT, flat panel display, plasma, etc. In some examples, the display screen 302 may additionally comprise a touch display. Further, the button pad 304 may be included with a plurality of buttons 306. The button 306 may allow a user to toggle through options displayed on the display screen 302. Thus, the button pad 304 may allow the user to interact with and manipulate the display screen 302.

Results from analysis of an image captured of the array 15 may be displayed on the display screen 302. As described above, the results from the analysis of an image of the array 15 may include a quantification of biomolecule expression levels. Thus, a concentration and/or amount of one or more antibodies, proteins, genes, etc. may be presented on the display screen 302. Since an infectious disease diagnosis may be inferred from antibody expression levels, an infectious disease diagnosis may additionally be presented on the display screen 302.

Thus, in the embodiment of the microarray assembly 10 shown in FIG. 3, the assembly 10 may be configured as a "one step" analyzer that upon input from the user via the display screen 302 and/or button pad 304, may both image the array 15, and analyze the the image by employing a method, such as the example method provided below with reference to FIG. 8. Specifically, a controller of the microarray assembly 10 (e.g., controller 34 shown in FIG. 1) may include computer readable instructions for executing a method, such as the method described below with reference to FIG. 8, to image the array 15 and/or analyze an image of the array 15, to provide an indication of biomolecule expression levels in the array 15.

In other words, in some examples, the microarray assembly 10 may be configured to perform both image acquisition and image analysis. By conducting both the image acquisition of the array 15, and analysis thereof, the microarray assembly 10 in the embodiment shown in FIG. 3, may determine concentrations and/or amounts of the target biomolecules (e.g., protein concentrations) in the array 15. These results may be displayed to the user via the display screen 302. Further, evidence of disease may be inferred and displayed to the user via the display screen 302 based on the concentrations of the target biomolecules. In this way, infectious disease diagnosis and identification may be performed by the microarray assembly 10 in certain embodiments.

Turning now to FIG. 4, it shows an external, exploded, perspective view 400 of a third embodiment of the microarray assembly 10 including the chip 12 and cuvette 13. Specifically, FIG. 4, shows the chip 12 and cuvette 13 detached from the microarray assembly 10 prior to insertion of the chip 12 and cuvette 13 into the assembly 10.

The cuvette 13 may comprise six or more walls, for enclosing the chip 12, when the chip 12 is inserted into the cuvette 13. Each of the walls may include an interior face (proximate to interior components of the microarray assembly 10) and an exterior (or outside) face, the exterior face visible to a user. Specifically, the cuvette 13 may comprise a front wall 406 with a front exterior face opposite from a back wall 408. Further, the cuvette 13 may comprise a first side wall 410 opposite from a second side wall 412, and a top wall (e.g., top face or surface) 416 opposite from a bottom wall (e.g., bottom face or surface) 414. The top wall 416 may include an aperture 418 for receiving the chip 12. Thus, the chip 12 may be inserted into the cuvette 13 through the aperture 418. The walls 406, 408, 410, 412, 414, and 416 of the cuvette 13 may be fluidically sealed along their edges, so that gasses, liquids, and/or solids may only enter or exit the cuvette 13 through the aperture 418. Specifically, the aperture 418 may include a mating groove 420 which may be configured to receive the chip 12. The groove 420 may be centered on the cuvette 13, for holding and retaining the chip 12. The edges of the chip 12, may fit into the groove 420, for inhibiting movement of the chip 12 relative to the cuvette 13.

In this way, the cuvette 13 may hold and retain the chip 12 at approximately the center of the optical beam produced by the laser 18 (shown above in FIG. 1). Further, the cuvette 13 may hold the chip 12 perpendicular to the optical beam produced by the laser 18 when inserted into the microarray assembly 10. The cuvette 13 may be constructed from any suitable material or combination of materials such as plastic, glass, acrylic, and stainless steel.

The door 214 of the microarray assembly may be adjustable between an open position to allow one or more of the chip 12 and cuvette 13 to be inserted into the assembly 10, and a closed position. Door 214 may be adjusted to a closed position during imaging of the chip 12. Specifically, when the door 214 is closed, the door 214 may be in sealing contact with the housing 201 of the assembly 10, so that substantially no light may escape from within the assembly 10 to outside the assembly 10. Thus, the door 214 may optically seal the interior and exterior of the assembly 10. In this way, laser light may not escape from the assembly 10, and light from exterior the assembly 10 may not pass into the assembly 10. As such, background noise may be reduced when imaging the array 15.

Further, the door 214 may include an electronic interlock which may enable the laser to be powered on, only when the door 214 of the microarray assembly is closed. In one example, as shown in FIG. 4, the electronic interlock may include a conductive rubber seal 404 positioned on an interior surface of the door 214. Further the interlock may include one or more metallic (e.g., stainless steel) pins 402 positioned on the assembly 10. When the door 214 is open, as shown in FIG. 4, the rubber seal 404 and pins 402 may not be in contact with one another, and as such power to the laser 18 may be inhibited. However, when the door 214 is closed, the rubber seal 404 may physically contact all of the pins 402, forming a complete series circuit. As such, power to the laser 18 may be enabled when the door 214 is closed, and the circuit of the electronic interlock is closed.

Figure 5:
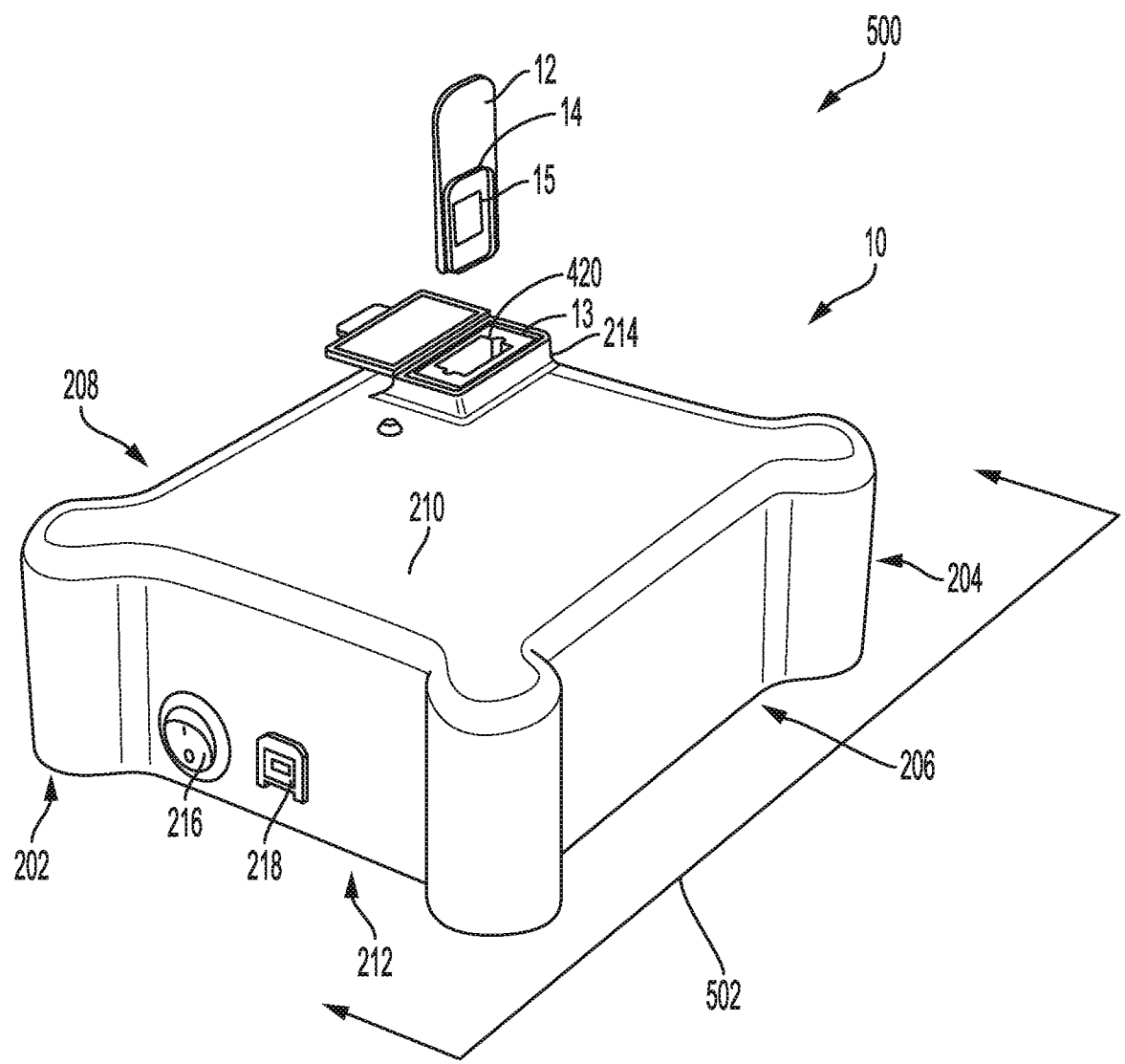
FIG. 5 shows an exploded view of the portable biomolecule microarray assembly of FIG. 2 including a microarray chip and a cuvette.

Turning now to FIG. 5, it shows an external, exploded, perspective view 500 of the microarray assembly 10 including the chip 12 and cuvette 13, where the cuvette 13 has been inserted into the assembly 10 through the door 214. Specifically, FIG. 5, shows only the chip 12 detached from the microarray assembly 10. Thus, as shown in FIG. 5, the cuvette 13 may be inserted into the assembly 10 prior to insertion of the chip 12 into the cuvette 13 and assembly 10. However, in other examples, it should be appreciated that the chip 12 may be inserted into the cuvette 13, prior to insertion of the cuvette 13 into the assembly 10.

In this way, the cuvette 13 may be removably coupled to the assembly 10. As shown above in FIG. 4, the cuvette 13 may be decoupled from the assembly 10, and as shown in FIG. 5, the cuvette may be inserted through the door 214 and recoupled to the assembly 10. The cuvette 13 therefore, may be inserted into the assembly 10, and then the chip 12 may be inserted into the cuvette 13. In this way, the cuvette 13 may retain and position the chip 12 within the assembly 10. Cutting plane 502 defines a cross section of the assembly 10 shown below in FIG. 6.

Moving on to FIG. 6, it shows a cross-sectional view 600 of the microarray assembly 10 taken along cutting plane 502 shown above in FIG. 5. Thus internal components of the microarray assembly 10 are exposed in FIG. 6. As such, FIG. 6, shows the relative positioning and orientation of the different components of the microarray assembly 10 with respect to one another. For example, FIG. 6 shows how the camera 30 and laser 18, may be positioned substantially parallel to one another. In this way, the camera 30 may be orientated so that the lens 31 points in the same direction as a light source end 602 of the laser 18 from which a laser beam is emitted from the laser 18.

Further, an axis system 605 is included in FIG. 6. Axis system 605 includes a horizontal axis 604 and a vertical axis 606. The axis system 605 may be used to describe the relative positioning of components of the microarray assembly 10. Components described as vertically above, may be positioned vertically above relative to the vertical axis 606. Thus, a first component described as vertically above a second component, may be positioned at a greater positive vertical point along axis 606 than the second component. Similarly components described as to the "right" or left" may be positioned to the right or left along the horizontal axis 604.

The laser 18 may be positioned vertically above the camera 30. However, the first dichroic mirror 22 may be positioned horizontally in line with the laser 18. Further, the second mirror 24 may be positioned horizontally in line with the camera 30. The first dichroic mirror 22, second mirror, and array 15 may be positioned vertically in line with one another. Thus, the first dichroic mirror 22, second mirror 24, and array 15, may be aligned along a line parallel to the vertical axis 606. Further, the first dichroic mirror 22, second mirror 24, and cuvette 13 including the array 15, may be horizontally offset from the laser 18 and the camera 30.

The cuvette 13 may include an optically clear window 608 positioned on the front wall 406 of the cuvette 13. The cuvette 13 may be orientated approximately perpendicularly to the laser 18, so that the front wall 406 including the window 608 faces a direction perpendicular to the direction of propagation of light emitted from the laser 18 before it reaches the first dichroic mirror 22. Said another way, the laser may be orientated so that the light source end 602 points towards the first dichroic mirror 22 in a first direction. The window 608 and wall 406 may face the first dichroic mirror 22 in a second direction, the second direction perpendicular to the first direction. The window 608 may allow light to pass relatively unobstructed through the cuvette 13. In this way, the laser beam reflected off the first dichroic mirror may pass through the window 608 to the array 15 (not shown in FIG. 6). Further, light emitted from the fluorescent labels of the array 15 may propagate out from the cuvette 13 through the window 608 back towards the first dichroic mirror 22 and the second mirror 24. As such, the cuvette 13 may be orientated in the assembly 10, so that the window 608 faces the first dichroic mirror 22 and the second mirror 24. The first dichroic mirror and second mirror 24 may be orientated at approximately a 45 degree angle with respect to the front wall 406 and window 608 of the cuvette 13. Further, the cuvette 13, may be orientated approximately perpendicular to the laser 18 and camera 30, so that light propagating from the array 15 out through the window 608, may travel in a direction perpendicular to the direction of light emitted from the laser 18 before it reaches the first dichroic mirror 22.

As shown in FIG. 6, the cuvette 13 may be positioned so that it is centered with and horizontally aligned with the first dichroic mirror. Further since the array 15 and chip 12, may be centered within the cuvette 13, the cuvette 13 may center the array 15 and chip 12 on a light beam produced by the laser 18 and reflected off the first dichroic mirror 22. In this way, the optically clear window and array 15 may be centered on the light beam produced by the laser 18. Further, the optically clear window 608 may be sized to permit relatively uniform light intensity dispersion across the surface area of the array 15.

Thus, the first dichroic mirror 22 and the second mirror 24 may be positioned at approximately a 45 degree angle relative to the laser 18, camera 30, and cuvette 13 including the chip 12 and array 15. Further, the cuvette 13 may be positioned perpendicular to the laser 18 and the camera 30 so that light passing in and out of the cuvette 13 may travel in a direction substantially perpendicular to the light passing between the laser 18 and the first dichroic mirror 22 and between the second mirror 24 and the camera 30. As such, light from the laser 18 may be reflected approximately 90 degrees towards the cuvette 13 including the array 15. Light emitted from the fluorescent labels of the array 15 may pass through the window 608 and first dichroic mirror 22 en route to the second mirror 24, where the light may be reflected approximately 90 degrees towards the camera 30 by the second mirror 24. Thus, light reflected from the second mirror 24 may travel opposite the direction of light emitted from the laser 18 towards the first dichroic mirror 22. In this way, the laser 18 and camera 30 may be orientated parallel to one another so that the light source end 602 of the laser 18 from which light propagates faces the same direction as the lens 31 of the camera 30.

Continuing to FIG. 7, it shows a perspective view 700 of the cuvette 13 and chip 12 prior to insertion of the chip 12 into the cuvette 13. In some examples, the cuvette 13 may be constructed from a suitable plastic material. However, in other examples, the cuvette 13 may be constructed from a plastic and glass. Specifically the optically clear window 608, which may be positioned on wall 406 may be comprised of glass, while the rest of the cuvette 13 may be constructed from plastic. In some examples, the optically clear window 608 may form all or a portion of wall 406, and as such may be integrally formed within the cuvette 13. However, in other examples, the window 608 may be formed separately from the cuvette 13 and may be attached to the cuvette 13. The glass that comprises the window 608 may be constructed from any suitable materials such as optically-clear glass, fused quartz, Aclar, and Topaz. Additionally or alternatively, other materials such as polystyrene and acrylic may be used in constructing the window 608.

All of the walls 406, 408, 410, 412, 414, and 416, may be fluidically sealed at their edges, to prevent gasses, liquids, or solids from entering the cuvette 13 other than through the aperture 418. As shown in FIG. 7 the groove 420 for accepting and retaining the chip 12, may be centered between walls front wall 406 and back wall 408. Further the aperture 418 and groove 420 may be centered between the side walls 412 and 410. In this way, the chip 12 may be centered along a central axis of the cuvette 13. The chip 12 may be removably coupled to the cuvette 13 via the groove 420. Thus the chip 12 may be inserted and removed from the cuvette 13 for cleaning and/or sterilization.

The nitrocellulose film 14 containing the array 15 (not shown in FIG. 7) may be positioned near a bottom of the chip 12, so that when the chip 12 is inserted into the cuvette 13, the film 14 is positioned more proximate the bottom wall 414 than the top wall 416 of the cuvette 13. The window 608 may be sized to permit light entering the cuvette 13 to reach the entire surface area of the film 14. As such, the size of the window 608 may be constructed based on the size of the film 14 and array 15.

FIG. 8 shows a flow chart of a method 800 for imaging an array (e.g., array 15 shown in FIG. 1) and analyzing images taken of the array to determine biomolecule expression levels in the array of a microarray assembly (e.g., microarray assembly 10 shown in FIGS. 1-6). The array may comprise a plurality of binding locations (e.g., binding locations 16 shown in FIG. 1) for binding biomolecules of a sample to the array. The array may be positioned on a nitrocellulose film (e.g., nitrocellulose film 14 shown in FIGS. 1 and 7), the nitrocellulose film forming a coating on a microarray chip (e.g., microarray chip 12 shown in FIGS. 1, and 4-7). Once biomolecules from the sample have been bound to the binding locations, the chip may be inserted into a chip cover (e.g., cuvette 13 shown in FIGS. 1, and 4-7) before being inserted into the microarray assembly. Once secured in the assembly, a laser (e.g., laser 18 shown in FIGS. 1 and 6) may be powered on to excite fluorescent labels chemically bound to a portion of the biomolecules on the binding locations. Specifically, a controller (e.g., controller 34 shown in FIGS. 1 and 6) may be in communication with the laser for adjusting operation of the laser. In response to excitation light from the laser, the fluorescent labels may emit light which may be captured in an image by a camera (e.g., camera 30 shown in FIGS. 1 and 6). The controller may send signals to the camera for capturing images of the array. In this way, the controller 34 may include computer readable instructions for executing a method such as method 800. As such, method 800 may be executed by the controller 34 based on input from a user via one or more of a computer (e.g., computer 122 shown in FIG. 1), display on the microarray assembly (e.g., display 302 shown in FIG. 3), or button pad on the microarray assembly (e.g., button pad 304 shown in FIG. 3).

In some examples, where the microarray assembly is configured as an image capturing device only, such as in the embodiment described above with reference to FIG. 2, the image acquired by the microarray assembly may be analyzed to determine biomolecule expression levels by a source external to the microarray assembly such as the computer. However, in other examples, where the microarray assembly is configured as both an image capturing and analysis device, such as in the embodiment described above with reference to FIG. 3, the controller of the microarray assembly may include computer readable instructions executable to both image the array, and analyze the image to determine biomolecule levels in the array.

Method 800 begins at 802 which comprises receiving user input. As described above, user input may be received by the controller from a touch display or button pad included on the microarray assembly. However, in other examples the user input may be received from a computer in communication with the controller of the microarray assembly via either a wired or wireless connection. The user input may include commands for one or more of: powering on or off the laser, taking a picture with the camera, and selecting one or more filters (e.g., filter 26 and 28 shown in FIGS. 1 and 6) for filtering pictures captured by the camera.

Method 800 may then continue to 804 which comprises determining if the chip is inserted into the microarray assembly. In one example, it may be determined that the chip is inserted if a door (e.g., door 214 shown in FIGS. 2-5) through which the chip is inserted into the assembly is closed. The position of the door may be determined based on a voltage and/or current output from a circuit included on an interior surface of the door. Thus, the current in the circuit may change depending on the position of the door. Specifically the current in the circuit may increase when the door is in a closed position relative to when the door is in an open position.

In another example, the method at 804 may comprise determining if the chip is inserted based on a state of a mechanical or electrical switch of the assembly. In some examples a bottom of the chip and/or chip cover may interface with the switch of the assembly, to transform the state of the switch. Thus, the state of the switch may change depending on whether the chip and/or cover is inserted into the assembly.

If it is determined that the door is open and/or that the chip is not inserted into the assembly, then method 800 may proceed to 806 which comprises not powering on the laser. In this way, the laser may only be powered on when the chip is inserted into the assembly, and the door of the assembly is closed to prevent light from escaping or entering the assembly during imaging of the array. Method 800 then returns.

However, if it is determined that the door is closed and/or that the chip is inserted into the assembly, then method 800 may continue to 808 which comprises turning on the laser for a duration and directing light emitted from the laser in a first direction towards a first dichroic mirror (e.g., first dichroic mirror 22 shown in FIGS. 1 and 6). The first direction may be a direction away from the laser and towards the first dichroic mirror (e.g., first direction shown by light propagation arrow 19a in FIG. 1). In some examples, the duration may be an amount of time. The duration may be a pre-set value stored in the memory of the controller. However, in other examples the duration may be adjustable based on input from the user. Thus, the user may adjust the amount of time that the laser is powered on. In still further examples, the duration may be based on the configuration of the assembly, such as the wavelength of light produced by the laser, intensity of the light beam produced by the laser, distance between the laser and the array, distance of the laser to a diffusing element (e.g., diffusing element 20 shown in FIGS. 1 and 6), type or wavelength of the fluorophore used in the probe molecules to fluorescently tag the target biomolecules, resolution and/or sensitivity of the camera, concentration or amount of biomolecules expressed or fluorescently tagged on the microarray chip, etc. Light emitted from the laser may propagate in a first direction towards the first dichroic mirror orientated at approximately a 45 degree angle to the direction of light propagation from the laser.

Method 800 then continues to 810 which comprises reflecting the light emitted from the laser towards the chip off the first dichroic and exciting the fluorescent labels in the array. Thus, in some examples, the method at 810 may comprise reflecting light approximately 90 degrees off the first dichroic mirror towards the array. Thus, the light traveling in the first direction may be reflected approximately 90 degrees so that after reflection it propagates in a second direction towards the array, the second direction perpendicular the first direction. For example, the second direction may be the same or similar to second direction shown above with reference to FIG. 1 by light propagation arrows 19b.

After exciting the fluorescent labels at 810, method 800 may then proceed to 812, which comprises reflecting light emitted from the array, specifically the fluorescent labels, off a second mirror (e.g., second mirror 24 shown in FIGS. 1 and 6) in a fourth direction (e.g., fourth direction shown by light propagation arrow 23b in FIG. 1) towards the camera. Light emitted from the array may be emitted in a third direction, the third direction being parallel but opposite the second direction and perpendicular to the first and fourth directions. For example, the third direction may be the same or similar to the third direction shown in FIG. 1 by emission light arrows 23a. In some examples the fourth direction may be opposite the first direction of light emitted from the laser towards the first dichroic mirror. Said another way, the fourth direction may be 180 degrees opposite the first direction. Thus, the method at 810 may include reflecting the light emitted from the array approximately 90 degrees towards the camera.

Light reflected off the second mirror may then be captured at 814. Thus, the method at 814 may comprise capturing an image of the array with the camera. Specifically, the controller may send signals to the camera for capturing an image of the array. In some examples, the camera may capture more than one image. Camera settings may in some example be pre-set, or in other examples, may be adjustable based on user input. The camera settings may include: a number of images to capture, filters, exposure duration, focal length of a lens (e.g., lens 31 shown in FIGS. 1 and 6), f-stop setting of the lens, camera gain, frame transfer speed, timing of the image acquisition relative to powering on of the laser, etc.

Additionally, digital information corresponding to the image may be acquired at 814. Specifically information corresponding to a location of each of a number of spots (e.g., spots 16 shown in FIG. 1) of the array may be acquired at 814. For example, a spot-by-spot delimited list of each spot's column and row placement in the assay, its name, ID, and its block location if the microarray is divided into individual print blocks may be acquired at 814. Further, the method 800 at 814 may comprise identifying images of the array that are rotated, inverted, and/or reversed. For example, the method 800 at 814 may comprise determining an angle of rotation of the image of the assay, which may be any angle between 0 and 360 degrees, and adjusting the orientation of the image so that it aligns with pre-set orientation conditions. Thus, at 814, the image acquired may be one or more of rotated and/or flipped (e.g., reflected across an axis) so that the orientation of the image acquired at 814 matches a pre-set orientation. Said another, during each successive iterations of method 800 (e.g., during multiple image acquisitions), each of the images of the one or more assays may be adjusted so that their orientation relative to one another is approximately the same.

One or more of the images taken at 814 may then be stored at 816. In some examples the images may be stored in non-transitory memory of the assembly such as on the controller and/or a storage device (e.g., memory chip 33 shown in FIG. 1). Additionally or alternatively, the method at 816 may comprise transferring the images taken at 814 to the computer for storage therein. In still further examples, the images may be stored in non-transitory memory of any suitable device for storing digital images such as a memory chip or card, flash drive, etc. Specifically information corresponding to the location of each of the spots of the array may be stored at 816. For example, the spot-by-spot delimited list of each spot's column and row placement in the assay, its name, ID, and its block location if the microarray is divided into individual print blocks may be stored at 816.

Thus, after storing the images at 816, the image capturing of the array may be complete. Said another way, the steps in method 800 up to and/or including 816 may be executed to capture and store an image of the array. As described above, in examples where the microarray assembly is configured as an image capturing device only, method 800 may return after storing the images at 816. Thus, in some examples, method 800 may return after storing the images at 816.

However, in still further examples, where the microarray assembly is configured as an image capturing device only, one or more images stored at 816 may be transferred to a source external to the microarray assembly, such as the computer for analysis to determine biomolecule levels in the array. The images may be transferred via a direct electrical connection between the microarray assembly and the external source, and/or may be transferred via the storage device. For example, a memory chip (e.g., memory chip 33 shown in FIG. 1) may be removed from the microarray assembly, and inserted into the computer or other external source, and the images contained on the memory chip may be uploaded to the external source. In yet further examples, the images may be transferred via a wireless connection such as Bluetooth, Wifi, or other electromagnetic wave frequency suitable for wirelessly transmitting data packets containing image data.

In examples, where the microarray assembly is configured as both an image capturing device and an image analysis device, such as in the embodiment described above with reference to FIG. 3, the controller of the microarray assembly may perform the analysis of the one or more images stored at 816 to determine biomolecule levels in the array.

Thus, in some examples, method 800 may continue from 816 to optional steps 818 and 820 which may be executed to perform the analysis of the one or more images stored at 816. It should be appreciated that in examples where the microarray assembly is configured as an image capturing device only, 818 and 820 may be executed by a source external to the microarray assembly (e.g., computer 122 shown in FIG. 1). Specifically, computer readable instructions may be stored non-transitory memory (e.g., data-holding subsystem 124 shown in FIG. 1) of the external source, where the instructions may be executable by a controller (e.g., logic subsystem 123 shown in FIG. 1) of the external source to perform a method such as 818 and 820 of method 800.

However, in other examples, where the microarray assembly is configured as both an image capturing and image analysis device, 818 and 820 may be executed by the controller of the microarray assembly.

Thus, method 800 may continue to optional step 818 which comprises determining the spot locations after storing the images at 816. Specifically, the spot location analysis performed at 818 may comprise identifying the location of each of the spots on the assay, including the biomolecules. The biomolecule expression levels at each spot may then be subsequently determined based on a wavelength analysis at 820 at described below. The spot location determination process may begin by acquiring the spot-by-spot delimited list of each spot's column and row placement in the assay, its name, ID, and its block location if the microarray is divided into individual print blocks. Information about the spot may be stored during image acquisition at 814 and image storage at 816 as described above. Based on an origin, a series of field points where each spot is expected to be located, may be determined.

Identification of the origin of the array (e.g., array 15 shown in FIG. 1) can be accomplished using an image recognition method. In the first method, a set of fiducial spots are printed onto a first row of binding locations (e.g., binding locations 16 shown in FIG. 1) of the array to serve as an image-recognition and alignment feature. The fiducial spots may be a pattern of spots separated by blanks, dilution series, or any other features that fluoresce. An image may be created of a first row of spots and that portion of the image may be saved as a recognition template. This template can be re-used for any microarray that has been printed with the same pattern of fiducials appearing in the first row. With this template as a guide, the corresponding pattern in each image the may be located and used in that subset of the image to identify the spot located at the origin, which may be the first row and column in the array. Once the origin is identified, the projected field points for all spots are calculated based on their coordinates derived from the image information stored at 816. If no recognition spots have been printed on the microarray, the first row of spots can serve as a surrogate recognition template for its own microarray image.

Subsequently, a series of measurements may be performed to identify the actual location of each spot. Using the calculated field points, a centroid of intensity located in a region surrounding each field point may be located. The centroid may be equivalent to the first moment of the spot region, defined as:

$$C = \frac{\sum_{p=1}^{N} I_p(\overline{X}_p + \overline{Y}_p)}{\sum_{p=1}^{N} I_p}$$

Where $I_p$ is the pixel intensity at the pixel p, $\overline{X}_p$ and $\overline{Y}_p$ are the distance vectors to the pixel p from an arbitrary reference location, and N is the total number of pixels in the region. Once the centroid is located, the field point is re-centered on the spot centroid. With this new location as an origin, the method may include locating inflection points in the gradient of intensity along vertical and horizontal lines through the region. These points may define the lines of steepest descent in the gradient of the signal, points that are directly related to the spot boundaries. At these inflection points, the gradient will be maximized and the second derivative of the intensity with respect to the radial coordinate will be zero:

$$\frac{\partial^2}{\partial r^2} I(r, \phi) = 0$$

Averaging the two inflection point locations along each axis provides the coordinates of the actual spot center. With this point as the new center, the method may then include searching for a circle of signal whose intensity is bounded by adjustable lower and upper limits relative to the local background. These limits define the sensitivity of the location algorithm relative to the background. A single sensitivity setting may be used for all images produced by a particular combination of spot diameter, print pitch, and assay protocol. The method may include keeping a running inventory of the calculated spot center and the actual spot centers during the microarray spot location routine. From the differences of these sets, adjustments for possible image rotation and drifts during the printing may be made. As such, the need to rotate or stretch a "grid" over the microarray to account for deviations in spot locations from their projected centers may be reduced or eliminated.

After determining the location of each of the spots at 818, method 800 may then proceed to 820, which comprises performing a wavelength analysis to determine the presence and/or levels of biomolecules at each spot. In some examples, only one wavelength of emitted light may be used for analysis at 820. Specifically, fluorescent tags of only one wavelength of light may be used to tag the target biomolecules. Thus, based on the emission intensities of the wavelength of light used to tag the target biomolecules, one or more of an amount, concentration, and/or level of the target biomolecules at each spot may be inferred. However, in other examples, the analysis at 820 may include multiplexing and analysis of two or more wavelengths of light, corresponding to two or more target biomolecules fluorescently tagged using different but simultaneously-excited labels. Put more simply, in examples where two fluorescent labels are used that have different wavelength emissions spectra, quantification of the intensity of each wavelength corresponding to the two or more labels may be used to determine biomolecule expression levels. In some examples, the light emitted by the different fluorescent tags may be sufficiently separated in wavelength, to discern the different tags. However, in some examples, various statistical algorithms, or data visualization software programs may be used to analyze the relative intensities of different wavelengths of electromagnetic waves emitted by the array and captured by the camera. In some examples, the analysis may include determining the presence and/or levels of antibodies. As such, the analysis at 820 may be used to diagnose an infectious disease. However, in other examples, the analysis may include determining the presence and/or levels of antigens. In still further examples, the analysis may include determining the presence and/or levels of one or more of DNA, RNA, peptides, etc. Thus, the method 800 at 820 may include generating results from the analysis, where the results may comprise an estimation of biomolecule levels/concentration in the array. Further the results may include an infectious disease diagnosis based on antibody concentrations/expression levels.

In some examples, method 800 may return after determining the concentration and/or levels of biomolecules in the array. However, in some examples, the method 800 may continue from 820 to 822 which comprises displaying the results via a display screen (e.g., display screen 302 shown in FIG. 3). Thus, estimations of biomolecule expression levels, (e.g., antibody, protein, antigen, DNA, and/or gene concentrations) derived from the analysis at 820 may be presented to via the display screen at 822. In this way, the method 800 at 822 may comprise displaying concentrations of one or more of antibodies, proteins, DNA, RNA, etc., and may additionally including displaying an infectious disease diagnosis. Method 800 then returns.

In this way, a microarray assembly may comprise a laser emitting in a first direction, a camera positioned parallel to and vertically below the laser, a first dichroic mirror horizontally aligned with the laser for reflecting light emitted from the laser, a second mirror horizontally aligned with the camera and vertically aligned with the first dichroic mirror, and a chip coated in a nitrocellulose film and including an array of wells containing one or more biomolecules. The camera mat further comprise a lens, and the camera may be orientated so that the lens is pointed in the first direction for capturing light reflected off the second mirror. In some examples, the assembly may further comprise a cover for housing the chip, the cover including one or more of an aperture and groove for receiving the chip. The cover may further include an optically clear window, the optically clear window integrally forming a front wall of the cover, where the front wall of the cover may be pointed towards the first dichroic mirror in a second direction, the second direction perpendicular to the first direction. The optically clear window described above may be sized to allow uniform light dispersal from the laser across a surface area of the array of wells containing the one or more biomolecules. The chip may be centered along a central axis of the cover, and the cover may center the array and optically clear window on a light beam produced by the laser. In some examples, the first dichroic mirror and the second mirror may be orientated at a 45 degree angle with respect to the lens of the camera and a light source end of the laser, from which a laser beam is emitted. Additionally or alternatively, first dichroic mirror and the second mirror may be orientated at a 45 degree angle with respect to the front wall of the cover. The microarray assembly may further comprise a door, adjustable between a closed position and an open position for receiving one or more of the chip and cover, where in the closed position, the door may optically and fluidically seal an interior and an exterior of the assembly. In some examples, the door may include an electrical circuit for monitoring the position of the door, where the voltage and/or current in the circuit may depend on the position of the door. In such a circuit, the current in the circuit may increase when the door is closed relative to when the door is open. Structurally, the cover may include 6 walls fully enclosing the chip, where the walls may be fluidically sealed at their edges, so that fluid communication between the interior and exterior of the cover is provided by the aperture only. The microarray assembly may be configured as a protein array and as such the one or more biomolecules may include one or more antibodies.

In another representation, a system for quantifying biomolecule expression levels may comprise a housing, a laser pointed in a first direction, a camera positioned parallel to and vertically below the laser, a first dichroic mirror horizontally aligned with the laser and orientated at a 45 degree angle with respect to a light source end of the laser for reflecting light emitted from the laser, a second mirror horizontally aligned with the camera and vertically aligned and parallel with the first dichroic mirror, a chip coated in a nitrocellulose film and including an array of wells containing one or more biomolecules, and a controller with computer readable instructions for capturing an image of light emitted from the array in response to excitation from the laser. In some examples, the one or more biomolecules may be tagged with a fluorescent label. The fluorescent label may comprise Quantum Nanocrystal fluorescent-nanoparticles. The system further of any of the above embodiments may further include a display screen for presenting images of the array captured by the camera to a user. An optical path length between the array and the camera may be approximately 120 mm.

In yet another representation, a method for imaging an array of a microarray assembly may comprise inserting the array into the microarray assembly, verifying the array is inserted in the microarray assembly, powering on a laser for duration and directing a laser beam produced by the laser in a first direction towards first dichroic mirror en route to the array, reflecting light emitted from the array in response to excitation from the laser off a second mirror in a second direction, the second direction opposite the first direction, and operating a camera to capture light reflected off the second mirror. The method may further comprise selecting one or more filters positioned between the camera and the second mirror for allowing only a desired range of wavelengths of light to reach the camera. Any of the above embodiments of the method may additionally or alternatively comprise identifying and locating each of a plurality of spots positioned on the array, where the spots may comprise one or more biomolecules chemically bound to the array. In any of the above embodiments of the method, the laser, camera, first dichroic mirror, and second mirror may be positioned in an optically folded arrangement, so that light emitted from the laser propagates in a parallel and opposite direction to light received by the camera.

In this way, a microarray assembly may include a laser for exciting fluorescent labels tagged to target biomolecules in a sample. Specifically, the fluorescent labels may include Quantum Nanocrystals fluorescent-nanoparticles (QNC). A laser beam produced by the laser may be reflected off a first dichroic mirror and directed towards an array to which the target biomolecules may be chemically bound. Laser light may reach the array via an optically clear window in a cover which houses a chip containing the array. When excited by the laser light, the fluorescent labels may emit light, which may propagate out from the cover through the optically clear window, back towards the first dichroic mirror. However, the first dichroic mirror may be optically transparent to light in the wavelength range emitted by the fluorescent labels, and as such light emitted from the fluorescent labels may pass through the first dichroic mirror and on to a second mirror. The second mirror may be configured to reflect substantially all wavelengths of light, and as such, light emitted from the fluorescent labels may be reflected towards a camera positioned in parallel with the laser. In this way, a lens of the camera used to gather light emitted from the fluorescent labels, and a light source end of the laser from which laser beam is emitted may face the same direction.

A first technical effect of increasing the compactness and therefore reducing the size of the microarray assembly is achieved by including both the first dichroic mirror and second mirror in series with one another so that the camera and laser may be positioned parallel to one another. By reducing the size of the microarray assembly, the portability of the assembly may be increased. In this way, the microarray assembly of the present invention may be transported and/or carried by a user.

Further, a second technical effect of increasing the resolution of images captured by the camera of the microarray assembly is achieved by utilizing QNC as the fluorescent labels of the biomolecules. By increasing the resolution of the images of the array, the accuracy of detections and/or quantifications of biomolecules present on the array may be improved. As such, the accuracy of infectious disease determinations may be increased.

Note that the example control and estimation routines included herein can be used with various microarray assembly configurations. The control methods and routines disclosed herein may be stored as executable instructions in non-transitory memory and may be carried out by the control system including the controller in combination with the various sensors, actuators, and other microarray assembly hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the microarray assembly system, where the described actions are carried out by executing the instructions in a system including the various microarray assembly hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to various microarray types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A microarray assembly comprising:
   a laser emitting in a first direction;
   a camera positioned parallel to and vertically below the laser;
   a first dichroic mirror horizontally aligned with the laser for reflecting light emitted from the laser;
   a second mirror horizontally aligned with the camera and vertically below the first dichroic mirror, wherein vertical and horizontal alignments of the camera, the laser, and the first and second dichroic mirrors are within a plane of a bottom wall of a housing encompassing the assembly; and
   a chip comprising a nitrocellulose film and including an array of wells on the nitrocellulose film, wherein the wells include one or more biomolecules.

2. The assembly of claim 1, wherein the camera further comprises a lens, and wherein the camera is orientated so that a centerline of the lens is pointed in the first direction for capturing light reflected off the second mirror.

3. The assembly of claim 2, where the first dichroic mirror and the second mirror are orientated at a 45 degree angle with respect to the lens of the camera and a light source end of the laser, from which a laser beam is emitted.

4. The assembly of claim 3, wherein the assembly further comprises a cover for housing the chip, the cover including one or more of an aperture and a groove for receiving the chip.

5. The assembly of claim 4, wherein the cover further includes an optically clear window, the optically clear window integrally forming a front wall of the cover, where the front wall of the cover is pointed towards the first dichroic mirror in a second direction, the second direction perpendicular to the first direction.

6. The assembly of claim 5, wherein the optically clear window is sized to allow uniform light dispersal from the laser across a surface area of the array of wells containing the one or more biomolecules.

7. The assembly of claim 5, wherein the chip is centered along a central axis of the cover, and wherein the cover centers the array of wells and the optically clear window on a light beam produced by the laser.

8. The assembly of claim 4, where the first dichroic mirror and the second mirror are orientated at a 45 degree angle with respect to a front wall of the cover.

9. The assembly of claim 4, wherein the assembly further comprises a door, adjustable between a closed position and an open position for receiving one or more of the chip and the cover, where, in the closed position, the door optically and fluidically seals an interior and an exterior of the assembly.

10. The assembly of claim 9, wherein the door and a top wall of the assembly form an electronic interlock; wherein the electronic interlock comprises a conductive rubber seal on an interior surface of the door and one or more metallic pins positioned in an opening for receiving one or more of the chip and the cover, and wherein the electronic interlock monitors a position of the door, where a voltage and/or a current in an electrical circuit formed by the electronic interlock depends on the position of the door.

11. The assembly of claim 10, wherein the one or more metallic pins are stainless steel, and when the door is closed, the rubber seal and the one or more metallic pins are in contact forming a complete circuit, and wherein a current in the circuit is increased relative to when the position of the door is open.

12. The assembly of claim 4, wherein the cover includes six walls fully enclosing the chip, where the walls are fluidically sealed at their edges, so that fluid communication between an interior and an exterior of the cover is provided by the aperture only.

13. The assembly of claim 1, wherein the one or more biomolecules comprise one or more antibodies.

* * * * *